United States Patent
Satake et al.

(10) Patent No.: US 6,683,970 B1
(45) Date of Patent: Jan. 27, 2004

(54) METHOD OF DIAGNOSING NUTRITIOUS CONDITION OF CROP IN PLANT FIELD

(75) Inventors: Satoru Satake, Tokyo (JP); Yukio Hosaka, Hiroshima (JP); Hideharu Maruyama, Hiroshima (JP); Nobuhiko Nakamura, Hiroshima (JP)

(73) Assignee: Satake Corporation, Tokyo (JP)

( * ) Notice: Subject to any disclaimer, the term of this patent is extended or adjusted under 35 U.S.C. 154(b) by 671 days.

(21) Appl. No.: 09/635,271

(22) Filed: Aug. 9, 2000

(30) Foreign Application Priority Data

Aug. 10, 1999 (JP) .............................. 11-226692
Aug. 12, 1999 (JP) .............................. 11-228761

(51) Int. Cl.⁷ .............................. G06U 9/00; G01V 3/00
(52) U.S. Cl. ........................... 382/110; 702/2; 356/402; 348/89
(58) Field of Search .............................. 382/110; 702/2; 356/402, 416, 413, 419, 418; 434/130, 150–153; 348/89

(56) References Cited

U.S. PATENT DOCUMENTS

| 4,371,081 A | 2/1983 | Satake |
| 4,429,225 A | 1/1984 | Fumoto et al. |

(List continued on next page.)

FOREIGN PATENT DOCUMENTS

| EP | 0443769 A2 | 8/1991 |
| EP | 0727260 | 8/1996 |
| EP | 0834731 A2 | 4/1998 |
| JP | 08015141 A | 1/1996 |

OTHER PUBLICATIONS

Nippon Shokuhin Kogyo Gakkaishi, "Applicability of Near Infrared Reflectance Method to Moisture, Protein and Ash Measurements of Buckwheat Flours", 1984, vol. 31, No. 3, pp. 200–202.

Nippon Shokuhin Kogyo Gakkaishi, "Near Infrared Reflectance Analysis for Determining Moisture, Protein and Ash Contents in Home–grown Wheat Flours", 1984, vol. 31, No. 1, pp. 50–53.

Primary Examiner—Bhavesh M. Mehta
Assistant Examiner—Aaron Carter
(74) Attorney, Agent, or Firm—Fish & Richardson P.C.

(57) ABSTRACT

A method of diagnosing nutritious condition of crop in a plant field is disclosed. The method comprises the steps of: locating a camera equipped with a plurality of image elements in a predetermined central depression angle with respect to the plant field; obtaining an amount of reflection light of a crop leaf for each image element by image-taking the field; obtaining an image-taken area for each unit image element by an area function constituted by a conversion variable including a ground clearance, an image element depression angle, the number of image elements and a field angle of the camera; making an area compensation of the amount of reflection light for each image element by the image-taken area; making a depression angle compensation of the amount of reflection light by a depression angle coefficient predetermined for compensating differences of amounts of reflection light correspondingly with image element depression angles; measuring an amount of light incident on the crop leaf; obtaining reflectance from the amount of the reflection light compensated and the measured amount of incident light; obtaining first crop information in a predetermined area based on the reflectance and a first crop related formula predetermined for obtaining crop information from reflectance, and storing the first crop information; and determining a nutritious condition of the crop in the plant field based on the first crop information. Instead of the grand clearance of the camera, a distance of field of view of the camera may well be used.

12 Claims, 10 Drawing Sheets

U.S. PATENT DOCUMENTS

| | | | |
|---|---|---|---|
| 4,630,736 A | 12/1986 | Maughan et al. | |
| 4,699,274 A | 10/1987 | Saika | |
| 4,742,228 A | 5/1988 | Bischoff | |
| 4,801,804 A | 1/1989 | Rosenthal | |
| 5,135,114 A | 8/1992 | Satake et al. | |
| 5,220,400 A | 6/1993 | Anderson et al. | |
| 5,254,858 A | 10/1993 | Wolfman et al. | |
| 5,258,825 A | 11/1993 | Reed et al. | |
| 5,353,053 A * | 10/1994 | Nishioka et al. | 348/33 |
| 5,371,358 A * | 12/1994 | Chang et al. | 250/226 |
| 5,389,781 A * | 2/1995 | Beck et al. | 250/226 |
| 5,412,219 A * | 5/1995 | Chappelle et al. | 250/461.1 |
| 5,443,164 A | 8/1995 | Walsh et al. | |
| 5,638,961 A | 6/1997 | Satake et al. | |
| 5,735,402 A | 4/1998 | Pezzoli et al. | |
| 5,764,819 A * | 6/1998 | Orr et al. | 382/110 |
| 5,841,883 A * | 11/1998 | Kono et al. | 382/110 |
| 5,845,229 A * | 12/1998 | Rawlins | 702/2 |
| 5,999,650 A * | 12/1999 | Ligon | 382/191 |
| 6,014,451 A * | 1/2000 | Berry et al. | 382/110 |
| 6,160,902 A * | 12/2000 | Dickson et al. | 382/110 |
| 6,178,253 B1 * | 1/2001 | Hendrickson et al. | 382/110 |
| 6,212,824 B1 * | 4/2001 | Orr et al. | 47/58.1 R |
| 6,366,681 B1 * | 4/2002 | Hutchins | 382/110 |
| 6,466,321 B1 * | 10/2002 | Satake et al. | 356/402 |
| 6,484,099 B1 * | 11/2002 | Holzer-Popp et al. | 702/2 |
| 6,529,615 B2 * | 3/2003 | Hendrickson et al. | 382/110 |

* cited by examiner ij

Aij

| NO① 3.8% | NO② 4.0% | NO③ 4.0% |
| --- | --- | --- |
| NO④ 3.6% | NO⑤ 4.2% | NO⑥ 4.0% |
| NO⑦ 3.6% | NO⑧ 4.0% | NO⑨ 3.8% |

| NO① 3.8→2.6 | NO② 4.0→2.8 | NO③ 4.0→2.8 |
|---|---|---|
| NO④ 3.6→2.4 | NO⑤ 4.2→3.0 | NO⑥ 4.0→2.8 |
| NO⑦ 3.6→2.4 | NO⑧ 4.0→2.8 | NO⑨ 3.8→2.6 |

METHOD OF DIAGNOSING NUTRITIOUS CONDITION OF CROP IN PLANT FIELD

BACKGROUND OF THE INVENTION

(1) Field of the Invention

The invention relates to a method of diagnosing nutrition of crop by obtaining crop information represented by nitrogen content, etc. of the crop from reflection light of the crop growing in a field. The invention also relates to a method of compensating the amount of reflection light obtained individually by a plurality of image elements.

(2) Description of the Related Art

A first conventional method for obtaining crop information such as a nitrogen content rate of a crop, a leaf color value, a nitrogen absorption amount, a plant height, a dry matter weight, etc., is one in which the amount of reflection light from the reference plate and the crop in the field is obtained by image-taking, by a light receiving means such as a digital camera, the reference plate which is coated with barium sulfate, etc. and the unit field (or a part of it) in which the crop grows, the reflectance of the crop is obtained from the amount of the light reflected from the reference plate and the crop, and the nitrogen content rate (amount of nitrogen absorption, a value of leaf color, a plant height, a dry matter weight) is obtained from the reflectance obtained and the relation formula predetermined for obtaining the nitrogen content rate (amount of nitrogen absorption, a value of leaf color, a plant height, a dry matter weight) from the reflectance, and the growth diagnosis has been conducted by comparing with a standard nitrogen content rate of that time period based on the number of growth days versus the nitrogen amount curve. However, the amount of reflection light of the crop to be obtained from the field is subject to change by weather. Also, even when the weather is compensated by the reference plate, it is necessary that each of the measuring direction, wind, and planting density be in the same condition as that applied when the predetermined relation formula was prepared for obtaining the nitrogen content rate from the reflectance. When the condition is different, the compensation is necessary accordingly, so that it cannot be said that all has been compensated only by obtaining the reflectance by the reference plate as reference. Actually, the measurement has been conducted under the limitation by the solar height, measuring direction, planting density or kind.

As for a second conventional method for obtaining crop information, there is an apparatus in which the light with a wavelength having relation to the crop information subject to increase or decrease depending on the growth of the crop, for example, the light ranging from a visible light region to a near infrared region is irradiated on a leaf blade of the crop and, based on the amount of the received light obtained with respect to the light with the wavelength having relation to the crop information and on the nitrogen amount related formula predetermined for calculating from the amount of light received, for example, a leaf blade nitrogen content, the leaf blade nitrogen content is measured. This apparatus is used to measure a number of leaf blades of the crop in the field and has enabled to obtain the leaf blade nitrogen content with a high precision. However, in order to grasp the crop information accurately for the overall field, a minute measurement extending to the overall field was indispensable, which is complicated and troublesome.

In the case where, as in the nutrition diagnosis of the crop leaf conducted according to the first conventional method, the so-called "remote sensing" is conducted and a comparatively large extent of field is subjected, the observation is made from quite far away so that there has occurred no large difference in areas of object corresponding to one image element of the camera. Therefore, there has occurred no difference in respective image elements in the resolution of the camera, either. On the other hand, in the "remote sensing" conducted quite close to the object, there occurs no large difference in areas of the object corresponding to one image element so that the measurement can be made in similar degree as above.

The first method described above is one in which, although the measurement is simple, the crop information to be obtained from the field is influenced by factors such as a measuring location and a planting density and, because of constraint in the measuring time and location, the method cannot be regarded as accurate. Also, when the camera is directed to the field and takes an image, the amount of reflection light obtained in each image-taking element of the camera has required compensation by a depression angle or field angle with respect to the field or a location such as this side or an opposite side in a large field. The distance between the camera and the field as the object varies for each image element, and the image-taking area obtained for each image element varies for respective distances. Further, the reflection angle differs by the depression angle and has an influence to the amount of reflection light. The second method, having no restraint in the measurement and having a high precision, is more advantageous than the first method. However, the problems in the second method are that the measurement has to be made for each leaf blade, thus requiring a large number of points to be measured and a long time accordingly.

The conventional remote sensing is conducted under the restrained condition that no large difference occurs in the area of the object for each image element. This is done for the reason of facilitating the subsequent compensation. However, because of the above restraint, a large scale observation means is required in order to enable taking an image of a large area and, if an image is taken extremely closely, the area of measurement becomes very small and it necessitates the measurements a plurality of times.

An object of the present invention is that, when obtaining the crop information by measuring the amount of reflection light, even though the camera is placed on the ground, compensation can be made so that no large error occurs, and a method of diagnosing nutrition of the crop provided is simple in the measurement of the crop information and enhances the measurement precision.

SUMMARY OF THE INVENTION

As a first method according to the present invention, the method of diagnosing nutrition of a crop in a field is arranged wherein: a camera equipped with a plurality of image elements is located in a predetermined central depression angle with respect to a field; an amount of reflection light of a crop leaf is obtained for each image element by image-taking the field; an image-taken area is obtained for each unit image element by an area function constituted by a conversion variable including a ground clearance of the camera, an image element depression angle, the number of image elements and a field angle; an area compensation is made of the amount of reflection light for each image element; a depression angle compensation is made of the amount of reflection light by the depression angle coefficient predetermined for compensating differences of amounts of reflection light correspondingly with image element depression angles; an amount of light incident on the crop leaf is measured; reflectance is obtained from the amount of the reflection light compensated and the measured amount of incident light; and crop information in a predetermined area based on the reflectance and a first crop related formula predetermined for obtaining the crop information is obtained and made first crop information. The first crop information is stored. By irradiating crop in the same area, an amount of at least either of transmission light or reflection light which is subject to increase and decrease depending on growth of the crop and which has a wavelength having relation to the crop information is measured, and crop information from the amount of light and a second crop related formula predetermined from the amount of light for obtaining crop information is obtained and stored as second crop information. The nutritious condition of the crop in the field is determined based on the first and second crop information.

The obtaining of the first crop related formula determined by obtaining the reflectance obtained from the amount of reflection light of the crop and the amount of reflection light for obtaining the first crop information in advance has been subject of research and is conventional. Also, the obtaining of the second crop related formula for obtaining the second crop information determined by obtaining the reflectance by irradiating the light on leaves has been subject of research and is conventional. Therefore, it is easy to obtain them individually. The present invention provides the method of diagnosing nutrition of the crop in which, for obtaining the first crop information, the difference in the amount of light caused by the difference in the light receiving area for each image element location of the camera having different image-taking ranges between the image element image-taken near by and the image element image-taken far away is compensated based on the image-taking angle between the so-called digital camera having a plurality of image elements provided in the field or based on, for example, the depression angle corresponding to the ground clearance of the camera which naturally occurs or on the field angle caused by the structure of the camera.

For the differences in the image-taking areas with respect to the amounts of light obtained for each unit image element, the specific (area) function for obtaining the area image-taken for each image element is determined by the secondary projection conversion by using the ground clearance of the camera and the accompanying depression angle for each image element, and the inherent coefficients of the camera such as the number of image elements which depends on the structure of the camera, the size of the image-taking elements which are aggregation of the image elements, and the angle of field which depends on the converging lens. Therefore, when the image-taken area for each image element is calculated by using the ground clearance and the depression angle as variables, or by adding the coefficients inherent to the camera as variables, and the amount of reflection light for each image element is divided by the image-taking area for each image element, it is possible to obtain the amount of reflection light for each image element which is not influenced by the image-taking area. In this way, the compensation relating to the distance between the camera and the image-taking location (this side or the opposite side) is realized.

Further, since there are a plurality of image elements, the depression angle is different for each unit image element. Thus, first, the image element in which the reference depression angle becomes, for example, 60°, and the compensation (depression angle) coefficient is made, for example, "1" is decided in advance. Then, while the depression angle is being varied, the reflection light amount at the same location of the crop field is measured for each depression angle and, from the varied amount of the reflection light amount based on the varied depression angle, it is possible to obtain the compensation coefficient at each depression angle. Based on the compensation coefficient, that is, the depression angle coefficient, obtained as above and the reflection light amount of each unit image element, the reflection light amount of each image element is compensated. In this way, it is possible to realize the compensation concerning the depression angles which vary by locations of the image elements.

At the depression angle which has been used as reference for the depression angle compensation in the above, the light amount of the natural light, that is, the light amount incident on the crop leaf may be calculated from the reflection light amount obtained by the reference reflection plate, and the reflectance of the image element can be calculated based on the amount of the natural light obtained as above and on the reflection light amount of the crop leaf obtained from the same image element. Similarly, by obtaining the reflection light amount for each image element, the reflectance of each unit image element can be obtained from the ratio with respect to the amount of the natural light. Further, it is also possible to calculate the reflectance from the ratio of the reflection light amount of the reference reflection plate and the reflection light amount of the unit image element.

The reflectance of the unit image element obtained as above is the reflectance of the unit image element obtained by the image-taking of the crop field by the camera on the ground, and is the reflectance in which any influence from the height or depression angle of the camera with respect to the crop field or from the structure of the camera has been compensated. Based on this reflectance and the reflectance of the crop leaves whose crop information is known, the first crop related formula determined in advance for obtaining the crop information from the reflectance is obtained by multiple regression analysis, and from the first crop related formula and the reflectance obtained by the compensation and the calculation explained above, it is possible to obtain the first crop information of the crop leaves. The wavelength of the amount of reflection light is not limited to 1, and the amount of reflection light at a wavelength necessary for obtaining the crop information is measured. Therefore, a task is necessary to obtain the reflectance for each of a plurality of wavelengths. For calculating respective functions or coefficients, it is possible to combine amounts of reflection light at a plurality of wavelengths.

In the method for obtaining the second crop information, the light which has a wave length having relation to the crop information subject to increase or decrease depending on the growth of the crop, for example, the light ranging from a visible light region to a near infrared region is irradiated directly on a leaf blade of the crop and, based on at least the reflection light amount or the transmission light amount obtained with respect to the light which has the wavelength having relation to the crop information and on the nitrogen amount related formula predetermined for calculating the leaf blade nitrogen content from the amount of light received by the crop leaves whose crop information, for example, a leaf blade nitrogen content is known, the leaf blade nitrogen content can be measured. This is embodied in an apparatus and is used to measure many leaf blades of the crop in the field and has enabled to obtain the leaf blade nitrogen content with a high precision. Thus, the method is useful in making a further compensation in the first crop information described above.

As a second method according to the present invention, the method of diagnosing nutrition of a crop in a field is arranged wherein: a camera equipped with a plurality of image elements is located in a predetermined central depression angle with respect to the field; an amount of reflection light of a crop leaf is obtained for each image element by image-taking the field; an image-taken area is obtained for each unit image element by an area function constituted by a conversion variable including a distance of field of view of the camera, an image element depression angle, the number of image elements and a field angle; an area compensation is made of the amount of reflection light for each image element; an image element depression angle compensation is made for the amount of reflection light by an image element depression angle coefficient predetermined for compensating differences in the amounts of reflection light according to the image element depression angles; an amount of light incident on the crop leaf is measured, reflectance is obtained from the amount of reflection light compensated and the above measured amount of light; and crop information in a predetermined area based on the reflectance and a first crop related formula predetermined for obtaining the crop information is obtained and made a first crop information. The method further comprises storing the first crop information, irradiating light on a leaf blade of the crop in the same area, measuring the amount of at least one of the transmission light and the reflection light which is subject to increase and decrease depending on growth of the crop and which has a wavelength having relation to the crop information is measured, obtaining crop information based on the amount of light and on a second crop related formula predetermined for obtaining the crop information from the amount of light and storing the crop information as second crop information, and diagnosing nutrition of the crop from the first crop information and the second crop information.

In this second method, in stead of the depression angle utilized for the specific function in the first method described above, the field distance of the camera is used. The specific (area) function for obtaining the area image-taken for each image element is determined by the secondary projection conversion by using the ground clearance of the camera and the accompanying depression angle for each image element, and the inherent functions of the camera such as the number of the image elements which depends on the structure of the camera, and the functions inherent to the camera such as the number of image elements which depends on the structure of the camera, the magnitude of the image-taking elements which are aggregation of the image elements, and the field angle which depends on the converging lens. Therefore, when the image-taken area for each image element is calculated by using the ground clearance of the camera and the field distance as variables, or by adding the coefficient inherent to the camera as variables, and the amount of reflection light for each image element is divided by the image-taking area for each image element, it is possible to obtain the amount of reflection light for each image element which is not influenced by the image-taking area. In this way, the compensation relating to the distance between the camera and the image-taking location (this side or the opposite side) is realized. With reference to the first crop information and the second crop information, how they are obtained has already been explained so that the explanation is not repeated here.

In the first and the second nutrition diagnosing methods explained above and the crop diagnosis to which such methods are applied, the first crop information may be obtained for each unit crop field, or may be obtained for each unit area which is arbitrary determined and which is smaller than the unit crop field. The unit crop field here refers to one field divided by what is normally called "furrow".

As a third method according to the present invention, the method of diagnosing nutrition of a crop in a field is arranged wherein: a camera equipped with a plurality of image elements is located in a predetermined central depression angle with respect to a field; an amount of reflection light of a crop leaf is obtained for each image element by image-taking the field; an image-taken area is obtained for each unit image element by an area function constituted by a conversion variable including a ground clearance, an image element depression angle, the number of image elements and a field angle; an area compensation is made of the amount of reflection light for each image element; a plurality of image elements are divided into sections based on the image-taken area of the unit image element corresponding to the maximum area among the image-taken areas obtained for each unit image element; reflectance is obtained from the amount of reflection light for each section and the amount of light incident on the crop leaf; and crop information in a predetermined area based on said reflectance and a first crop related formula predetermined for obtaining the crop information is obtained and made the first crop information, and nutrition of the crop is diagnosed from said first crop information.

The present invention provides the method of diagnosing nutrition of the crop in which, for obtaining the first crop information, the difference in the amount of light caused by the difference in the light receiving area for each image element location of the camera having different image-taking ranges between the image element image-taken near by and the image element image-taken far away is compensated based on the image-taking angle between the so-called digital camera having a plurality of image elements provided in the field or based on, for example, the depression angle corresponding to the ground clearance of the camera which naturally occurs or on the field angle caused by the structure of the camera.

Since the way as to how the differences in the image-taking areas with respect to the amounts of light obtained for each unit image element is the same as in the first method explained above, no explanation is repeated here.

Further, according to the third method of the invention, a plurality of image elements are divided based on the image-taking area of the unit image element corresponding to the maximum area among the plurality of the image elements. When the camera is directed to the crop field, the crop field area which is obtained by one image element becomes larger as the camera is far from the crop field. Thus, the division is worked out by using the maximum area of the crop field area obtainable by one image element as reference and, for forming the same area, other image elements are combined. That is, even though the numbers of image elements are different, the crop field area divided is the area of constant size for obtaining the reflected light. In this case, the maximum area of the crop field area which can be obtained by one image element is made the reference. The amount of the reflection light can be obtained at the constant area so that, when the camera is placed on the ground, even when there are differences in the crop field areas obtained for respective image elements, they can be divided into the constant areas, thus enabling to obtain the amount of the reflection light which has no influence to the resolution by the camera.

On the other hand, according to the fourth method, the reflectance is sought, of the image-taken areas obtained for each of the unit image elements, from the amount of reflection light of the unit image element below the predetermined image-taken area and the amount of light incident on the crop leaf. When the camera is directed to the crop field, the field area obtainable by one image element becomes larger as the camera is further away. Therefore, the information from the image element image-taken of a field area exceeding the area predetermined as appropriate for the nutrition diagnosis of crop leaves is unaccepted, and only the information from the image element image-taken of a field area below the predetermined area is treated as acceptable. And, by using the predetermined area of the crop field obtained by one image element as reference, other image elements are combined so as to be the same divided area in size. That is, even though the number of image elements differs, the image elements are so divided as to form the predetermined same size area of the crop field for purposes of the amount of reflection light. The reference at this time is a predetermined crop field area. Since the amount of reflection light can be obtained with respect to the predetermined area, the camera may be placed on the ground, and the crop field areas obtained for respective image elements may differ, but the areas may be divided into the predetermined area. In this way, it is possible to obtain the amount of reflection light which has no influence to the resolution of the camera. The predetermined area here is meant for the crop field area which is appropriate for the nutrition diagnosis of the crop leaves, for example, in the order of 1 $m^2$ to 5 $m^2$.

By calculating the ratio between the amount of reflection light from the fixed area or the predetermined area obtained as explained above and the amount of reference reflection light of the reference plate or the amount of light incident on the crop leaf by solar light, the calculated ratio is made a reflectance for the fixed area or the predetermined area.

The reflectance of the fixed area or the predetermined area obtained as above is the reflectance obtained by the image-taking of the crop field by the camera on the ground, and is the reflectance in which any influence from the height or depression angle of the camera with respect to the crop field or from the structure of the camera has been compensated. Based on this reflectance and the reflectance of the crop leaves whose crop information is known, the first crop related formula determined in advance for obtaining the crop information from the reflectance is obtained by multiple regression analysis, and from the first crop related formula and the reflectance obtained by the compensation and the calculation explained above, it is possible to obtain the first crop information of the crop leaves. The wavelength of the amount of reflection light is not limited to 1, and the amount of reflection light at a wavelength necessary for obtaining the crop information is measured. Therefore, a task is necessary to obtain the reflectance for each of a plurality of wavelengths. For calculating respective functions or coefficients, it is possible to combine amounts of reflection light at a plurality of wavelengths.

As a fifth method according to the present invention, in the method of diagnosing nutrition of a crop in a field, a camera equipped with a plurality of image elements is located in a predetermined central depression angle with respect to a field; an amount of reflection light of a crop leaf is obtained for each image element by image-taking the field; an image-taken area is obtained for each unit image element by an area function constituted by conversion variables including a field distance of the camera, an image element depression angle, the number of image elements and a field angle; an area compensation is made of the amount of reflection light for each image element; a plurality of image elements are divided into sections based on the image-taken area of the unit image element corresponding to the maximum area among the image-taken areas obtained for each unit image element; reflectance is obtained from the amount of reflection light for each section and the amount of light incident on the crop leaf; and crop information in a predetermined area based on said reflectance and a first crop related formula predetermined for obtaining the crop information is obtained and made first crop information, and nutrition of the crop is diagnosed from said first crop information.

In this fifth method, in stead of the depression angle utilized for the specific function in the first method described above, the field distance of the camera is used. That is, with reference to the difference in the image-taking area with respect to the amounts of the light obtained for each image element, the specific (area) function for obtaining the area image-taken for each image element is determined by the secondary projection conversion by using the ground clearance of the camera and the accompanying field distance (distance between the image element and the image-taking point) for each image element, the number of the image elements and the inherent functions of the camera such as the number of image elements which are based on the structure of the camera and the magnitude of image-taking elements which are the aggregation of the image elements, and the field angle, etc. which is based on the converging lens. Therefore, when the image-taken area for each image element is calculated by using the ground clearance and the field distance of the camera as variables, or by adding the coefficient inherent to the camera as variables, and the amount of reflection light for each image element is divided by the image-taken area for each image element, it is possible to obtain the amount of reflection light for each image element which is not influenced by the image-taken area. In this way, the compensation relating to the distance between the camera and the image-taking location (this side or the opposite side) is realized. Among the image-taken areas of unit image elements, the maximum area is used as reference, and other image elements are divided for obtaining the fixed area in dimension. In this respect the explanation made in the third embodiment applies and the same explanation is not repeated here.

According to a sixth method of the invention, a method of diagnosing nutrition of crop in a field is arranged wherein: a camera equipped with a plurality of image elements is located in a predetermined central depression angle with respect to a field; an amount of reflection light of a crop leaf is obtained for each image element by image-taking the field; an image-taken area is obtained for each unit image element by an area function constituted by a conversion variable including a field distance of the camera, an image element depression angle, an image element number and a field angle; an area compensation is made of the amount of reflection light for each image element; reflectance is obtained from the amount of reflection light of the unit image element which becomes smaller than the predetermined image-taken area among the image-taken areas obtained for each unit image element and the amount of light incident on the crop leaf; and crop information in a predetermined area based on said reflectance and a first crop related formula predetermined for obtaining the crop information is obtained and made first crop information, and nutrition of the crop is diagnosed from said first crop information.

In the sixth method of the invention, in stead of the depression angle utilized for the specific function in the fourth method, the depression angle is used. For the differences in the image-taking area with respect to the amounts of light obtained for each image element, the specific (area) function for obtaining the area image-taken for each image element is determined by the secondary projection conversion by using the ground clearance of the camera and the accompanying depression angle for each image element, and the inherent functions of the camera such as the number of the image elements which depends on the structure of the camera, and the functions inherent to the camera such as the number of image elements which depends on the structure of the camera, the magnitude of the image-taking elements which are aggregation of the image elements, and the field angle which depends on the converging lens. Therefore, when the image-taken area for each image element is calculated by using the ground clearance and the depression angle as variables, or by adding the coefficient inherent to the camera as variables, and the amount of reflection light for each image element is divided by the image-taking area for each image element, it is possible to obtain the amount of reflection light for each image element which is not influenced by the image-taking area. In this way, the compensation relating to the distance between the camera and the image-taking location (this side or the opposite side) is realized. When the crop field area obtained is smaller than the predetermined area, the unit image elements are adopted, and the adopted image elements are divided for forming the predetermined area. The method of dividing is the same as that explained for the fourth method and the explanation is not repeated.

For obtaining the second crop information, the light which has a wave length having relation to the crop information subject to increase or decrease depending on the growth of the crop, for example, the light ranging from a visible light region to a near infrared region is directly irradiated on a leaf blade of the crop and, based on at least one of the amount of the reflection light and the amount of the transmission light obtained with respect to the light which has the wavelength having relation to the crop information and on the nitrogen amount related formula predetermined for calculating the amount of nitrogen content in the leaf blade from the amount of light in the crop leaf whose crop information, for example, the amount of nitrogen content in the leaf blade is known, the amount of nitrogen content in the leaf blade can be measured. This apparatus is used to measure many leaf blades of the crop in the field and is able to obtain the leaf blade nitrogen content with a high precision. Thus, it is effective to compensate further the first crop information described above.

An effective method for compensation by the combination of the two useful methods for obtaining the above explained first crop information and second crop information is explained hereunder. The difference between the first crop information and the second crop information obtained respectively is first calculated. By using this difference for compensating the first crop information, it is possible to compensate not only the errors caused by weather changes (weather, time, solar position) but also the errors caused by changes in cultivation factors (measuring direction, planting density) which have heretofore been considered difficult to be compensated. This method is especially suited for conducting nutrition diagnosis at a plurality of spots in the same field because the determination for the compensation is simple and easy.

Where the difference between the first crop information and the second crop information decided as above is stored, only by obtaining the first crop information from the unknown crop in the fixed area in the field from which the first crop information has been obtained, it is possible to compensate the first crop information by the first crop information and the above difference. This method enables the easy compensation of the errors caused by the planting density and the measuring direction, and the method may be embodied in an apparatus with the compensation value being provided. Such apparatus can be readily used for crop nutrition diagnosis.

For conducting a more strict compensation than in the first to fourth crop nutrition diagnosing methods, the following method is applied. That is, after the first crop information is obtained and divided into a plurality of divisions, at least two points of data from within the plurality of divisions are selected, and the second crop information is obtained directly from the crop leaves in the same field as the field from which the two points of data are selected. Thus, from the two points of data of the first and the second crop information, the correlation thereof is determined and the compensation conversion formula is defined and, based on this formula, all the values in the plurality of divisions are compensated. In obtaining the compensation conversion formula, the plurality of crop information can be obtained from the fixed extent of area and, further, from the compensation conversion formula, the first crop information can be compensated for a large extent of area.

For conducting a compensation in the first to fourth crop nutrition diagnosing methods, there is another method as follows. In the field exposed to natural light, the reflectance of the light that has wavelength having relation to the crop information subject to increase or decrease depending on the growth of crop is measured and, based on the reflectance and the first crop related formula predetermined for obtaining the crop information from the reflectance, the crop information for each division is obtained and stored. Then, from the first crop information stored in the respective divisions, the crop information in at least two divisions is selected, and the light is irradiated on the crop leaf blades from the two divisions of the field and the amount of at least transmission light or reflection light having relation to the crop information subject to increase and decrease depending on the growth of the crop is measured. Then, based on the amount of light and the second crop related formula predetermined for obtaining the crop information from the amount of light, the crop information from the two section is obtained and stored, and the compensation conversion formula for compensating the first crop information based on the second crop information is determined and is made third crop information after compensating the first crop information for each division by the compensation related formula. The third crop information thus obtained may be used for nutritious diagnosis of the crop in the field.

This method obtains the information relating to the plurality of divisions individually. The data of at least two divisions are selected from among the plurality of divisions and, by obtaining the second crop information directly from the crop leaves from the same divisions as the divisions from which data in the two divisions are obtained, the correlation between the first crop information and the second crop information is determined by the data of the two points and the compensation conversion formula is defined. Based on this formula, all the values of the plurality of divisions can be compensated. In obtaining the compensation conversion formula, the plurality of crop information can be obtained from a large extent of area and, further, from the compensation conversion formula, the first crop information can be compensated for a large extent of area.

In the diagnosing methods described above, the first crop related formula and the compensation conversion formula are stored and the reflectance from the crop leaves of unknown fields is measured whereby, based on the first crop related formula and the compensation conversion formula, the third crop information can be obtained. Where these items are stored in a memory section of a control means and are used for appropriate operation, the method can be realized as an apparatus which, not only realizes the diagnosing of the crop but also contributes in enhancing the precision in the measurement.

The arbitrary two divisions to be selected from among the plurality of divisions may be divisions of the maximum value and the minimum value, respectively, from the first crop information. In this way, the straight line in the compensation conversion of the first crop information and the second crop information can be determined readily at the two points, high and low, without being affected by the remaining data.

There can be various crop information but, for purposes of diagnosing nutrition of the crop, the nitrogen content of leaves or the color values of leaves are considered to be the best. This is understandable from the fact that, in the crop, the nitrogen content in leaves is the factor which immediately shows the effectiveness of the fertilization or whether the fertilization is appropriate or not.

In the above crop diagnosing methods, in order to measure the reflectance of the light which has wavelength having relation to the crop information subject to increase or decrease depending on the growth of the crop, the reflectance of the crop is image-taken by the image-taking elements constituted by a plurality of image elements, the image elements having received the reflection light corresponding to the crop are selected, and the reflectance is measured based on the light received data of the selected image element, thereby providing a method of diagnosing the crop by obtaining the first crop information. The reflection light obtained by an image-taking means such as a digital camera is influenced by the planting density or the dimension of the image-taken field, for example, whether the unit field is within the extent of 1 m², so that the light image-taken of the crop as the reflection light is not necessarily the reflection light. That is, from the stand point of the unit image element, the reflection light from other than the crop, for example, the light reflected from the soil of the field may be included. Thus, it is desired that only the image elements which relate to the reflectance of the predetermined extent of area be selected and be used as the reflection light from the crop, and the first crop information be obtained based on such data of the received light.

BRIEF DESCRIPTION OF THE DRAWINGS

The above and other objects, features and advantages of the present invention will be apparent from the following description of preferred embodiments of the invention explained with reference to the accompanying drawings, in which.

PREFERRED EMBODIMENTS OF THE INVENTION

Figure 1:
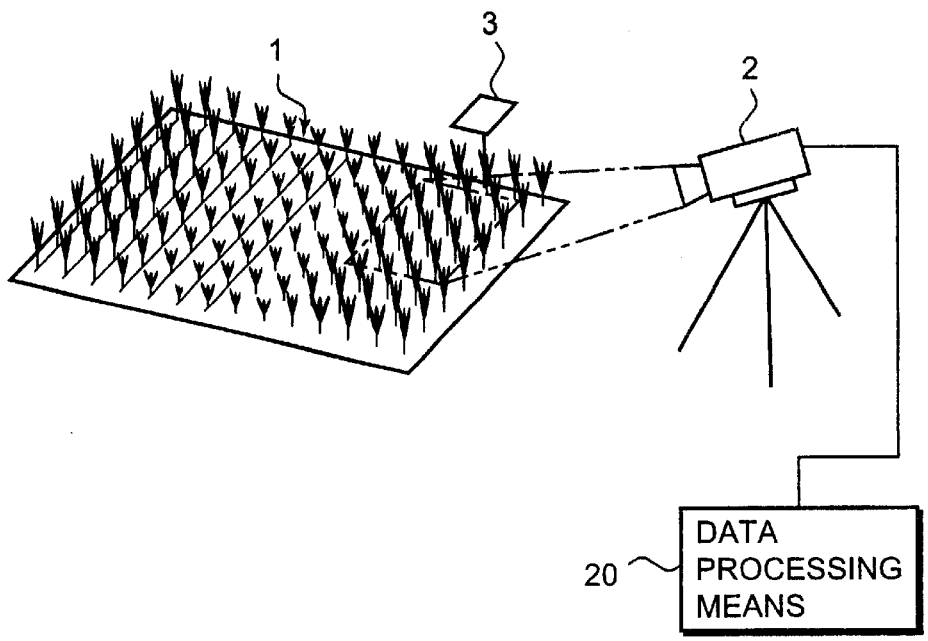
FIG. 1 is a sketch showing locations of a camera and a reference plate disposed in a field for measuring reflection light of a crop.

The measuring method according to the present invention is explained with reference to FIG. 1 through FIG. 3. Here, the rice plant is used as an example of crop. A camera 2 which is a light receiving means for measuring reflection light from the crop is directed to a field 1 in which the crop is growing. The field 1 is of course exposed to the natural light. Also, the reference plate 3 in white color is disposed in the crop field 1.

Figure 2:
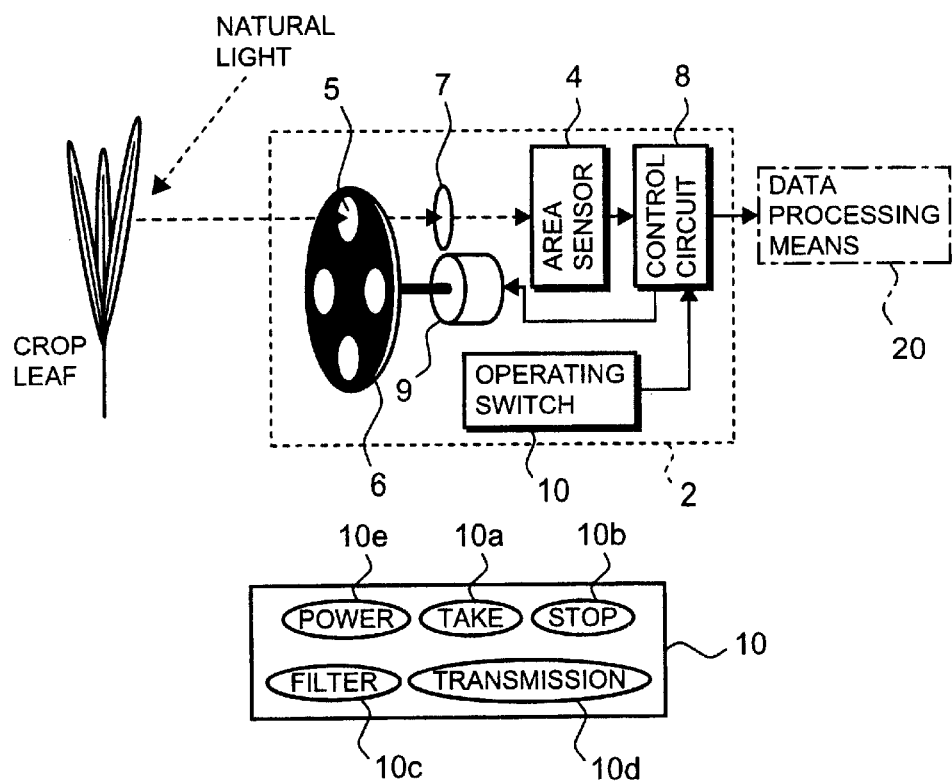
FIG. 2 is a block diagram of the camera for measuring reflection light of the crop.

FIG. 2 is a block diagram showing the camera 2. The camera 2 has a resolving power in the order of 240,000 (600×400) and is equipped with an area sensor 4. In the camera 2, there is a filter wheel 6 equipped with a plurality of narrow band filters 5, and the filters 5 are switched by rotating, for example, the filter wheel 6. The light having passed the filter 5 is received by the area sensor 4 via, for example, a converging lens 7 as a optical means. The filter wheel 6 is rotated by a stepping motor 9 whose driving force is controlled by a control circuit 8. Further, the control circuit 8 forwards a signal of the received light from the sensor 4 to the data processing means 20.

The filters 5 are suitably selected from among visible light wavelengths of 450, 550, 625, 650, 675 and 700 nm., and also from among near infrared region wavelengths of 750, 850, 950–1300 nm. As to these wavelengths, it is necessary to select regions which show characteristic changes caused by changes in nitrogen content rates or color values of leaves of the crop. Thus, the filters may be selected from both visible light wavelengths and near infrared region wavelengths, or may be selected from either of them. Further, the wavelengths are not limited to those in the embodiment of the invention. FIG. 2 shows 4 filters, but the number of filters is not limited and is changeable and may be changed according to the intended purposes. To the control circuit 8, there is connected an operating switch 10 and, to the operating switch 10, there are connected an image-taking starting switch 10a for starting the image-taking, an image-taking stopping switch 10b for stopping the image-taking, a filter switching switch 10c for switching the filters, a data transmission switch 10d for transmitting image-taken data, and a power switch 10e.

Figure 3:
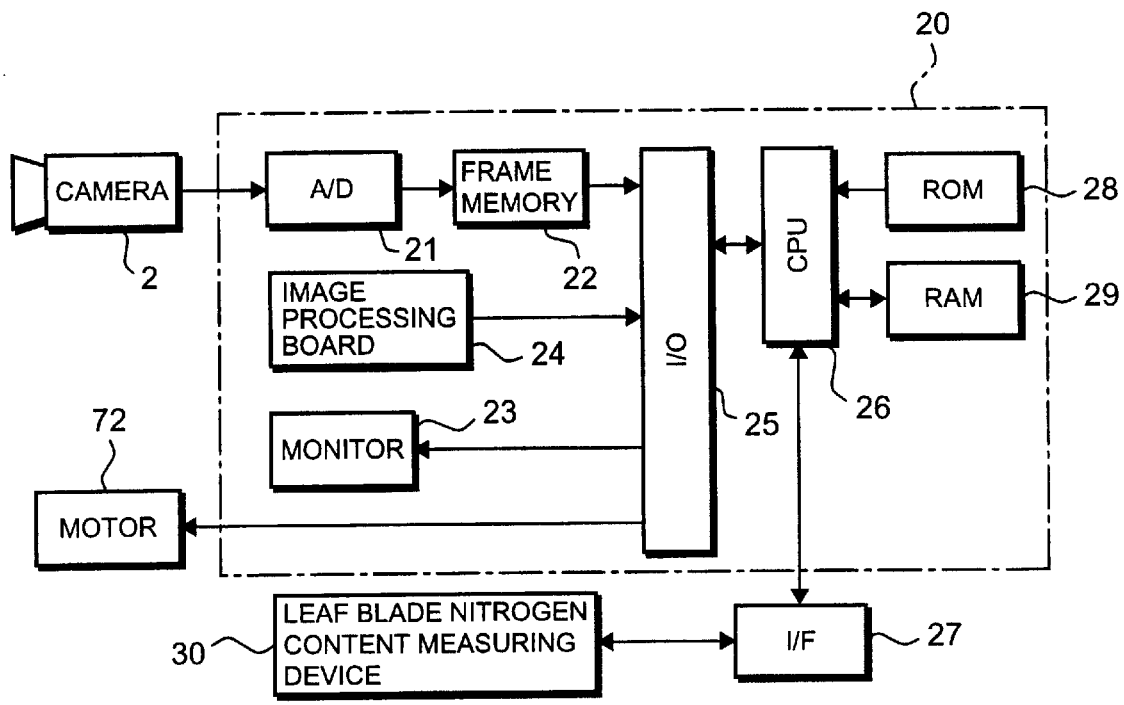
FIG. 3 is a block diagram of a data processing means.

FIG. 3 shows, in a block diagram, a data processing means 20. The data processing means 20 shown in FIG. 3 is equipped with an analog/digital converter (hereinafter referred to as "A/D converter") 21, a frame memory 22 for storing image data after the A/D conversion, a monitor 23 for visually showing the image data, and a digital image processing board 24. These are in communication with a CPU 26 which arithmetically processes the image data through an input/output port (hereinafter referred to as "I/O port") 25, and are connected to a leaf blade nitrogen content measuring means 30, explained later, via an interface board (hereinafter referred to as "I/F board") 27. Also, to the CPU 26, there are connected a read only memory (hereinafter referred to as "ROM") 28 in which a control program, etc. is stored, and a read and write memory (hereinafter to as "RAM") 29 which enables the storing of the calculated results and the reading of them as desired.

When the power switch 10e of the camera is pressed, the reflection light signal of the image is received by the area sensor 4 and becomes the image signal and, when the data transmission switch 10d is pressed, this image signal is transmitted to the data processing means 20. At the data processing means 20, the image signal is processed by the image processing board 24 and the processed image appears on the monitor 23. At the monitor 23, while the field 1 is being confirmed, the location of the camera is set and the extent of the image-taking is determined. Once the extent of the image-taking is determined, the leaves of the rice plant growing in the field 1 is image-taken by pressing the image-taking starting switch 10a through the filter 5 presently set, and then the filter switching switch 10c is switched whereby a signal is outputted from the control circuit 8 for the stepping motor 9 and the filter wheel 6 to be rotated. After the switching of the filter 5 by the rotation of the filter wheel 6, the image-taking is performed by pressing the image-taking switch 10a. Consequently, the image signal is produced for each filter 5. Here, if the area sensor 4 of the camera 2 lacks a large capacity of memory elements, the data transmission switch 10d is pressed every time the image is taken for the data to be transmitted to the data processing means 20.

Figure 4:
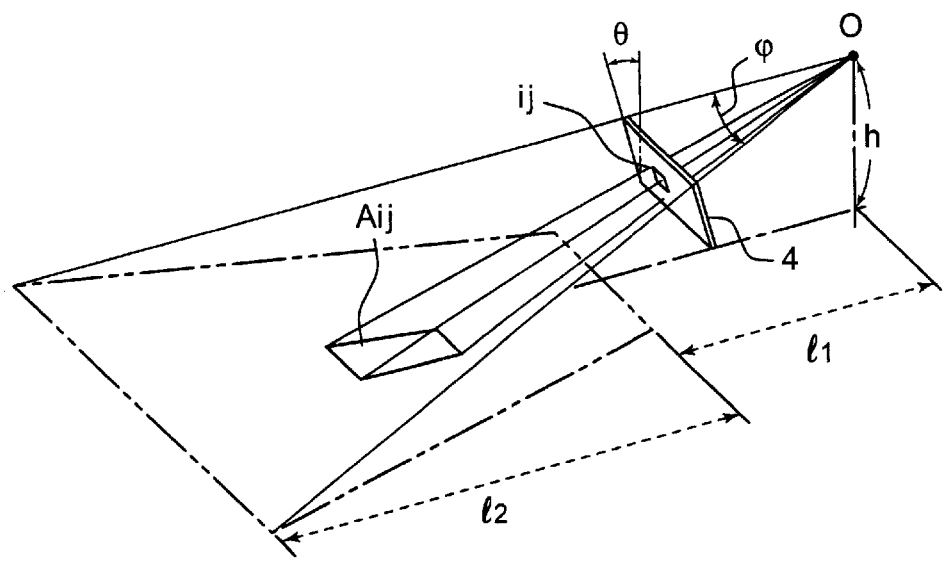
FIG. 4 is a diagram showing a depression angle and a field angle when the crop field is image-taken.
Figure 5A:
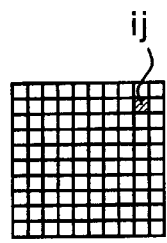
FIG. 5 is a diagram showing a coordinate of an image element and an image taken area by an image sensor.
Figure 5B:
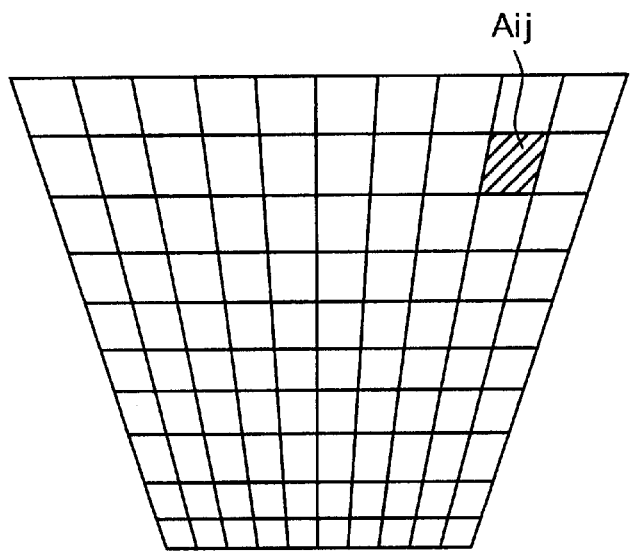

The data of the unit image element image-taken by the camera 2 of the measuring means as constructed above is processed as explained hereinafter. FIG. 4 is a diagram of a field when image-taken by the camera 2 from the observing point "O" with the ground clearance from the camera 2 being "h", the depression angle being "θ", the field angle being "φ", the field distance being "$l_1$", "$l_2$" etc. Further, FIG. 5(a) shows an image element coordinate ij of the area sensor 4, and FIG. 5(b) shows a crop field area obtained by the image elements. As is clear from FIG. 5, the crop field image obtained by each image element coordinate ij has areas which are different respectively. Therefore, even within the same crop field, the density of the amount of information is different in each image element coordinate ij. This difference is compensated by the area function given below. The area function here means what is generally called a secondary projection conversion, and since this is a mathematical analysis, only the outline thereof is explained herein. From the ground clearance height "h" from the camera 2 or the crop field distance "l", the depression angle "θ" of the image-taking, the field angle "φ" which is an inherent coefficient of the camera 2, and the number of image elements, the following area function can be established.

(Depression Angle)

$$Aij = f(\theta, h, i, j, x1, x2 \ldots) \ldots ①$$

(Crop Field Distance)

$$Aij = g(\theta, 1, i, j, x1, x2 \ldots) \ldots ② \quad (1)$$

Aij: Crop field actual area obtained by ij
i,j: Image element coordinate
x1: field angle (inherent to camera)
x2: number of image elements (inherent to camera)

When the depression angle "θ" and ground clearance "h" or crop field distance "l" are given, the actual area Aij for each image element coordinate can be calculated. That is, from either the crop field actual area 1-① calculated based on the depression angle or the crop field actual area formula 1-② calculated based on the crop field distance, the actual area can be obtained.

Here, when the reflection light (intensity) amount at the image element coordinate ij is made Pij, then $$P'ij = Pij/Aij \quad (2)$$

stands, so that the amount of the received light Pij obtained by the image element ij is divided by the actual area Aij, the reflection light amount per unit area which is not influenced by the size of the crop field actual area obtained by the image element coordinate ij is obtained. As above, the area compensation can be made for each image element coordinate ij, and it is possible to obtain the reflection light amount for each image element coordinate ij which is not influenced by the size of the actual area obtained by the image-taking. The forgoing has explained the area compensation by the secondary projection conversion in the case where the image-taking is performed at the predetermined ground clearance "h" or the crop field distance "l", or the predetermined depression angle "θ".

Figure 6:
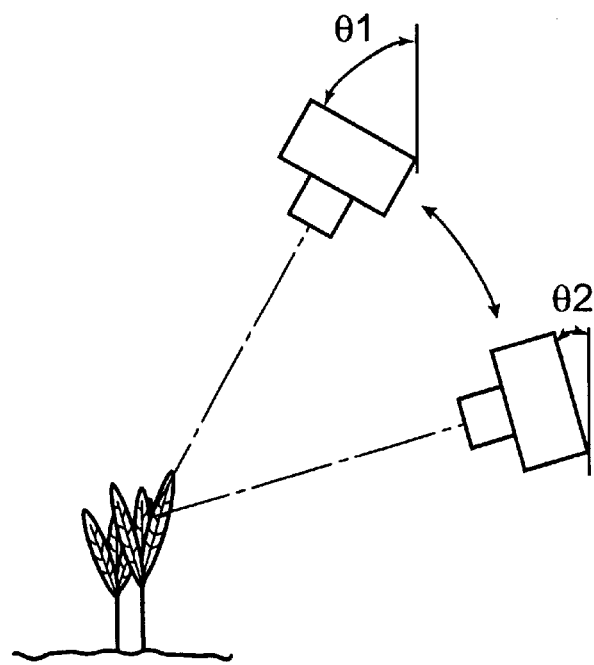
FIG. 6 is a sketch showing the image-taking for determining a compensation coefficient for compensating the depression angle.

Next, since the depression angle "θ" is different for each image element coordinate ij, the depression angle compensation accompanying the depression angle "θ" is made. As in FIG. 6, the reflection light of the reference plate or the reflection light of the crop leaf at the same location in the field is measured at the same distance. For example, the depression angle "θ1" is changed to the depression angle "θ2" and, preferably by the reflection light amount of the image element coordinate at the center portion of the area sensor 4, the compensation function may be determined. For example, the compensation function of the reflection light amount at 60° of the depression angle "θ" may be set to K60°=1.

Depression angle θ=60°: K60°=1

Depression angle θ=50°: Reflection light amount at Depression angle 50°/Reflection light amount at Depression angle 60°= Compensation coefficient at Depression angle 50=K50°

Depression angle θ=40°: Reflection light amount at Depression angle 40°/Reflection light amount at Depression angle 60°= Compensation coefficient at Depression angle θ40°=K40°

Depression angle θ=10°: Reflection light amount at Depression angle 10°/Reflection light amount at Depression angle 60°= Compensation coefficient at Depression angle θ10°=K10° (3)

may result, so that the compensation coefficient at each depression angle "θ" is defined, and the compensation coefficient Kij of each image element coordinate ij is defined. Therefore, by P'ij obtained after the above mentioned area compensation and the compensation coefficient Kij, P"ij=Kij·P'ij (4)

may result, and the depression angle compensation by the depression angle "θ" can be made. The above has explained the compensation relating to the depression angle "θ". In any case, it is necessary that, in the area compensation, the predetermined values (θ, h, l etc.) be inputted in advance, or in the depression angle compensation, the reflection light amount be measured by a plurality of depression angles "θ" and the compensation coefficient Kij be defined in advance.

The reflection light amount received by the area sensor 4 of the camera 2 is the reflection light amount of the reference plate 3 and the reflection light amount of the crop leaf in the field 1. When the reflection light amount of the reference plate 3 is measured, the depression angle "θ" used as reference in the depression angle compensation, the reference plate reflection light amount at the depression angle 60° in the above example, may preferably be measured. When the reference plate reflection light amount measured as above, on the assumption that it is the amount of light incident on the crop leaf, is assumed to be PO, Rij=P"ij/PO (5)

Rij: Reflectance for each image element coordinate ij

Thus, the reflectance of rice crop leaves can be obtained. This reflectance is utilized for calculating the nitrogen content in the rice crop leaves. These Formulas 1 through 5 are stored in ROM 28. The above mentioned reference plate reflection light amount PO is measured and stored in the following ways. The filters 5 which the camera 2 is equipped with are switched and the reflection light amount of the reference plate 3 is measured for each filter and the measured data is transmitted to the data processing means 20 where the data is digitally converted by the A/D converter 21 and stored in RAM 29. That is, the value of the reflection light amount PO of the reference plate is measured at each filter 5 and is stored.

By the camera 2, the filters 5 are switched and, at each filter, the reflection light amount of the leaves of the rice crop in a certain range in the field 1 is received and transmitted to the data processing means 20. At the data processing means 20, the signal is digitally converted by the A/D converter 21 and is stored in the frame memory 22. At the CPU 26, with respect to the reflection light amount of the leaves at each filter 5 stored in the frame memory 22, the average value of the reflection light amount received by each image element is obtained, and the reflectance is calculated based on the above mentioned Formulas stored in advance in ROM 28 with the calculated result being stored in RAM 29. In this way, the reflectance of the crop leaves in a certain range, for example, within 1 square meter, by unit image element is stored.

Figures 7, 8:
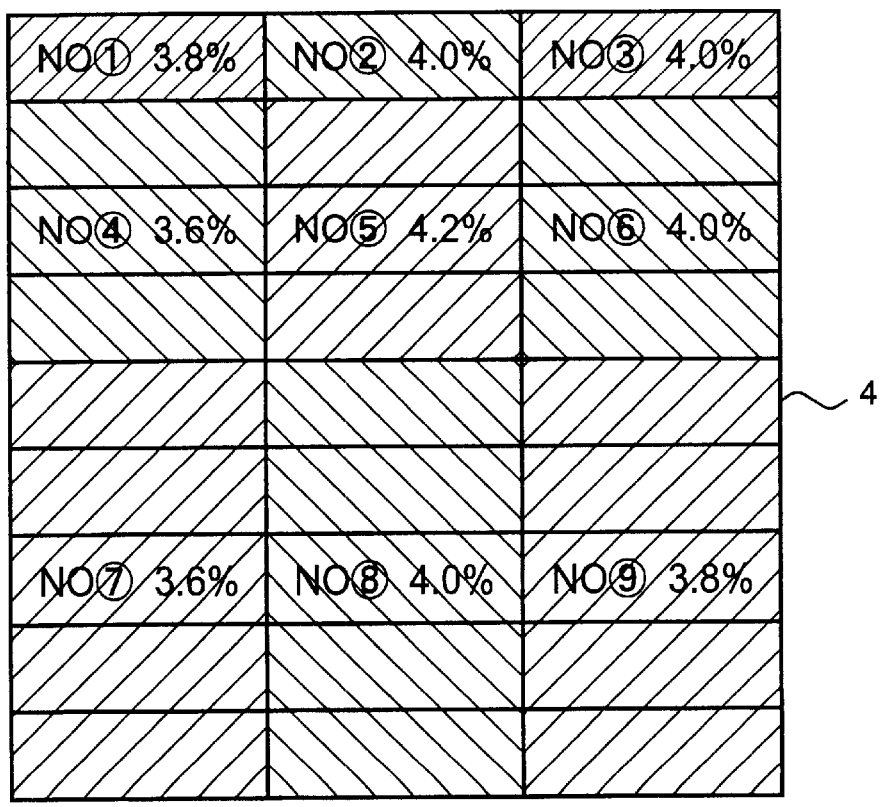
FIG. 7 is a table showing nitrogen contents in divisions which are divided by a fixed area and by the reflection light obtained from the field.
FIG. 8 is a table showing nitrogen contents in divisions which are divided by a fixed area and by the reflection light obtained from the field.

FIG. 7 shows an example wherein the data of 240,000 pixels image-taken of the crop leaves in the field 1 is further divided into a plurality of divisions. For example, by the camera 2, the filters 5 are switched and, at each filter, the reflection light amount of the leaves of the rice crop in a certain range in the field 1 is received and transmitted to the data processing means 20. At the data processing means 20, the signal is digitally converted by the A/D converter 21 and is stored in the frame memory 22. At the CPU 26, with respect to the reflection light amount of the leaves at each filter 5 stored in the frame memory 22, the divisions Nos. ①–⑨, for example, from the left hand top in FIG. 7 are made, and the average value of the reflection light amount received by each image element 2 is obtained. Then, based on the above mentioned Formulas stored in advance in ROM 28, the reflectance for each division of the 9 divisions is calculated and stored in RAM 29. If the extent in which one camera receives the light is assumed to be, for example, 1 m², the reflectance of the 9 divisions within 1 m² is stored. At the monitor 23, the image having been processed by the image processing board 24 is displayed.

Figure 9:
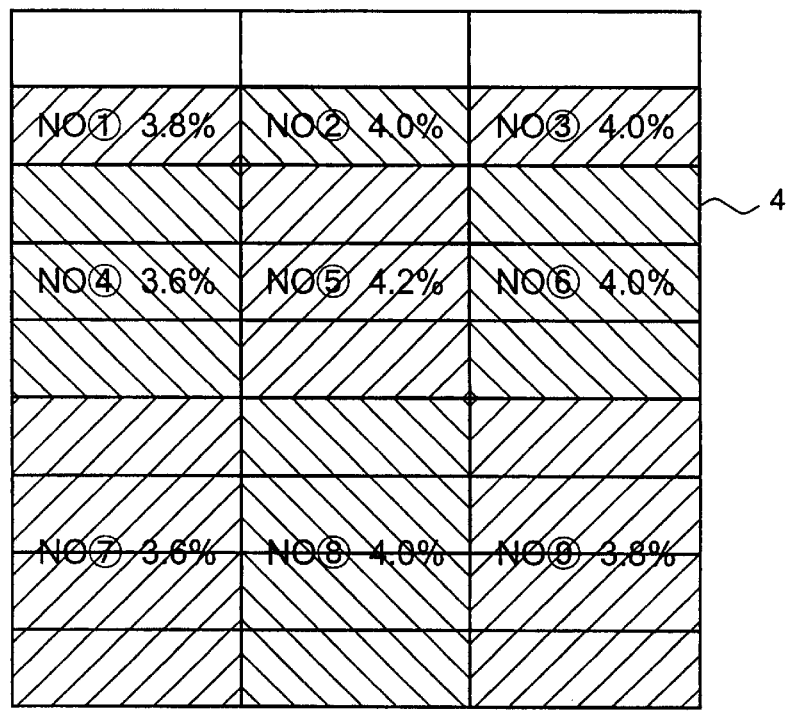
FIG. 9 is a table showing nitrogen contents in divisions in which the areas smaller than the predetermined area are selected based on the reflection light obtained and which are divided by the predetermined area.

FIGS. 8 and 9 show the second example wherein the data of 240,000 pixels image-taken of the crop leaves in the field 1 is divided into a plurality of divisions. The divisions in this second example are decided in the manner explained hereinafter. First, in the first method of making the divisions as shown in FIG. 8, the crop field actual area of the image element (in FIG. 8, each of ①–③) showing the maximum value from among the field actual areas Aij obtained by unit image element image-taken of the crop field is set as reference, that is, this maximum crop field actual area is used as reference area, a plurality of image elements adjacent thereto are combined so that all the image elements are divided into the divisions of the same area. In this case, even when the unit image element is required to be further divided, since the reflection light amount per unit area has been calculated, and the reflection light amount per unit area can be reflected to the divided area, it is possible to obtain the divisions of the same area. In this way the divisions are made and, in the present example, there are 9 divisions for the convenience sake. That is, the image elements ①–③ at the top portion of FIG. 8 are respectively regarded as maximum areas and, with these actual areas as reference areas, if the remaining image elements are divided into the divisions of the same area, the 3 image elements ④–⑥ and the 5 image elements ⑦–⑨ become the divisions of the same area. In actuality, divisions become more complicated, but they are shown here in a simplified form. Preferably, the image-taking by the camera is performed so that the predetermined area becomes 1 m² to 5 m². When the division is made with a unit being smaller than the above, the information of the crop leaves is not reflected to all the reflection light amount obtained for each image element due to such factors as a large size crop leaf or a planting density, and also working efficiency is lowered. Conversely, if the division is too large, the working efficiency is assisted, but the information to be obtained is not sufficient and the measuring precision is affected.

In the second method of making divisions as shown in FIG. 9, among the crop actual areas Aij obtained by unit image elements image-taken of the field, only the predetermined area, for example, the image elements not exceeding 1 m² (image elements not included in divisions ①–⑨) is selected, and a plurality of image elements adjacent thereto are combined so that all the image elements are divided into the divisions of the same area. In this case, even when the unit image element is required to be further divided, since the reflection light amount per unit area has been calculated, and the reflection light amount per unit area can be reflected to the divided area, it is possible to obtain the divisions of the same area. In this way the divisions are made and, in the present example, there are 9 divisions for the convenience sake. In FIG. 9, the three image elements at the top portion are excluded as exceeding the predetermined area and, among the image elements smaller than the predetermined area, the divisions ①–③ become exactly the predetermined area, the three image elements ④–⑥ together become the predetermined area, and the four image elements ⑦–⑨ together become the predetermined area. In actuality, divisions become more complicated, but they are shown here in a simplified form. Preferably, the image-taking by the camera is performed so that the predetermined area becomes 1 m² to 5 m². When the division is made with a unit being smaller than the above, the information of the crop leaves is not reflected to all the reflection light amount obtained for each image element due to such factors as a large size crop leaf or a planting density, and also working efficiency is lowered. Conversely, if the division is too large, the working efficiency is assisted, but the information to be obtained is not sufficient and the measuring precision is affected.

In the RAM 29, the reflectance of the crop leaves within the extent of the light received through each of a plurality of filters 5 and the reflectance of the crop leaves respectively processed in the 9 divisions by each filter 5 are stored. The reflectance in each filter 5 stored in RAM 29 or the reflectance processed in the 9 divisions by each filter 5 are made explanatory variables and, by collecting the leaves growing within the same extent of the light received or within the same division, the crop information from these leaves, e.g., the nitrogen content directly analyzed, or the color value obtained by directly measuring the color of the leaves, the nitrogen content rates or the color values are made objective valuables. Then, the relation formula for obtaining the crop information of the crop leaves within the extent of the light received and the relation formula (first crop related formula) for obtaining the crop information of the leaves of the crop for each of the 9 divisions are prepared and stored in ROM 28.

Further, assuming that there exist reflectance R1 by the filter 1 at the division No.①, reflectance R2 by the filter 2, reflectance R3 by the filter 3, and reflectance R4 by the filter 4, and there exists a nitrogen content rate N1 obtained by chemically analyzing the crop leaves within the division, then $$N1 = F0 + F1 \cdot R1 + F2 \cdot R2 + F3 \cdot R3 + F4 \cdot R4 \qquad (6)$$

stands and, by measuring a plurality of nitrogen content rates N, $$N1 = F0 + F1 \cdot R11 + F2 \cdot R21 + F3 \cdot R31 + F4 \cdot R41$$

$$N2 = F0 + F1 \cdot R12 + F2 \cdot R22 + F3 \cdot R32 + F4 \cdot R42$$

$$\ldots$$

$$Nn = F0 + F1 \cdot R1n + F2 \cdot R2n + F3 \cdot R3n + F4 \cdot R4n \qquad (7)$$

stands and, if the multiple regression analysis is made, then $$N = F0 + F1 \cdot R1 + F2 \cdot R2 + F3 \cdot R3 + F4 \cdot R4 + C \qquad (8)$$

N: nitrogen content rate of the measured subject
F0~F4: constant
R1~R4: reflectance of each filter
C: compensation value may be used to calculate the related formula (first crop related formula). For leaf color values, too, the related formula may be obtained similarly. This Formula 8 is stored in the ROM 28.

As above, if the Formula 1 through the Formula 5 and the Formula 8 are stored and, by image-taking by the camera 2 the reference plate and the leaves of the rice crop within the extent of the light received, and transmitting the image signal to the data processing means 20, the nitrogen content rate can be calculated based on the first crop related formula at the data processing means 20. In this way, the nitrogen content rate in the rice crop within the extent of the light received or the nitrogen content rate (first crop information) in each division, i.e., No.①–⑨ can be obtained. The values given in each division in FIG. 7 are examples of the nitrogen content rates obtained as above.

Figure 10:
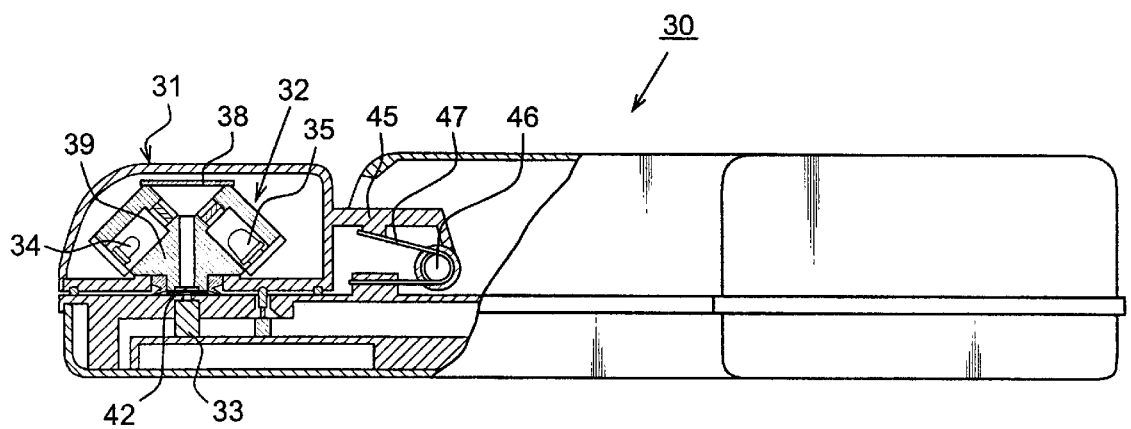
FIG. 10 is a sectional view, partially broken, of a main portion of a leaf blade nitrogen content measuring means.
Figure 11:
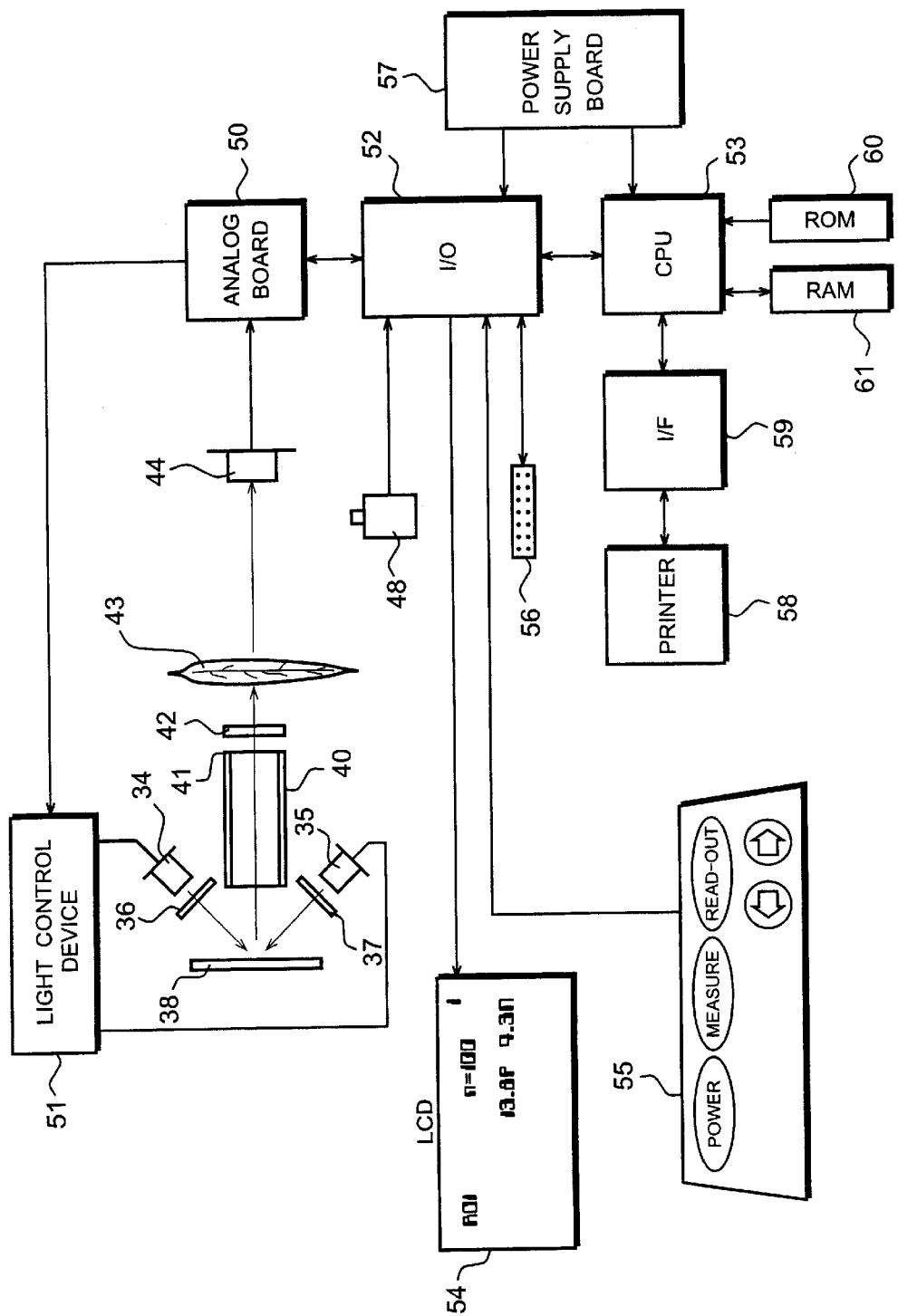
FIG. 11 is a control block diagram of the leaf blade nitrogen content measuring means.
Figure 12:
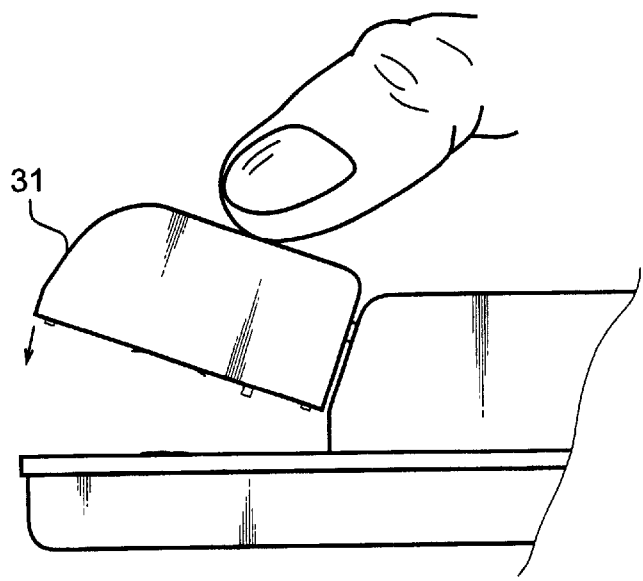
FIG. 12 is a diagram showing operation of the leaf blade nitrogen content measuring means.

Next, an example of the leaf blade nitrogen content measuring device 30 is explained with reference to FIG. 10 to FIG. 12. There the main portion of a portable type nitrogen content measuring device (hereinafter referred to as "measuring device") 30 is shown in a partly broken sectional view. The device shown in FIG. 10 and FIG. 11 is constructed such that, within the body 31, there are provided a light source section 32 and, at a lower part, photodiodes (not shown) which constitute a light amount detection device 33. As the light source 32, LEDs 34, 35, i.e., a plurality of light emitting elements having different wavelength peaks on the same periphery are provided, and narrow band filters 36, 37 respectively having different wavelength bands are provided to the LEDs 34, 35. As the wavelength bands, 500 nm–1100 nm are preferred and, from these wavelength bands, the narrow band filters 36, 37 having relation to the leaf blade nitrogen content obtained from these wavelength bands or an arbitrary specific wavelength having relation to the color values of leaves are selected. The light emitted from each of the LEDs 34, 35 becomes the light having the specific wavelengths by the narrow band filters 36, 37, and is incident on a diffusion reflection plate 38 at which the light is reflected. Further, a block 39 is formed so that the light from each of the LEDs 34, 35 is incident on the diffusion reflection plate 38 in substantially the fixed angle.

The light reflected at the diffusion reflection plate 38 is incident in a reflection light path 40 provided in the center of the block 39, and then is incident on the diffusion transmission plate 42 provided on the radiating side 41 of the reflection light path 40. The diffusion reflection plate 42 is provided perpendicular to the optical axis of the reflection light path 40, and is formed of frosted glass or milky white glass. Through the space surrounded by the reflection light path 40 and the diffusion reflection plate 38, the light passes out of the reflection light path 40 while repeating the reflection and the diffusion, and is incident in the light amount detection device 44 through the diffusion transmission plate 42 and via the leaf 43 being measured.

Further, on the top periphery of the light amount detection device 32, a top cover 31 is surroundingly provided, and the arm 45 extending from the top cover 31 is pivotally supported by the axis 46. Also, the axis 46 pivotally supporting the top cover 31 carries a coil spring 47 for the top cover 31 to be constantly urged upwardly. That is, as will be understood from FIG. 12, in conducting the measurement, the leaf 43 may be inserted into the measuring portion, and the pressing down of the top portion of the top cover 31 enables the measuring operation. The timing at which the measuring is made is when, by the pressing down of the top cover 31, the pressing-down projection (not shown) presses a micro-switch 48 provided at the opposite position thereof, and the measuring (light irradiation and light amount measurement) is performed by detecting the pressing-down of the top cover 31.

Next, a light absorbency device 30 shown in a block diagram in FIG. 11 is explained. The transmission light amount of the sample leaf 43 detected at the measuring section constituted by the light source section 32 and the light amount detection device 33 is converted to analog signals by the light amount detection device 44. The light source section 32 is provided with the light emitting means 51 of LEDs 34, 35. At the analog board 50, either the A/D conversion from analog to digital signals, or the V/F conversion from voltage to frequency is performed. The signals converted are inputted through the I/O board into the CPU board 53 which serves as an arithmetic and control means. In the I/O board 52, there are provided a liquid crystal display device LCD 54 for displaying the results of the calculation or operational instructions, an input section 55 for carrying out operation, a connecting port 56 of RS232C for inputting or outputting data from and to the outside means, and a switch 48. To these CPU board 53 and I/O board 52, the power supply board 57 is connected for the power to be supplied. Also, the printer 58 is connected to the CPU board 53 via a printer I/F board 59. Further, to the CPU board 53, a read-only memory (hereinafter referred to as "ROM") 60 and a read and write memory (hereinafter referred to as "RAM") 61 are connected. In the ROM 60 are stored a plurality of calibration curves on a field to field basis or a kind (breed) to kind basis. The calibration curves constitute a relation formula (second crop related formula) for obtaining the nitrogen content rate (second crop information) determined in advance, wherein absorbency is calculated from a plurality of the received amounts of the light obtained by irradiating the light on a plurality of leaves for which the nitrogen content rates are measured in advance, and the multiple regression analysis is conducted by using the absorbency as explanatory variable and a plurality of known nitrogen content rates as objective variables. As to the multiple regression analysis, the procedures with which the above Formulas are obtained have already been explained so that no explanation is repeated here. Further, ROM 60 stores a series of programs, which execute operations from the measuring and calculation of the absorbency to the displaying of the calculation results, for measuring the absorbency at the measuring means 30 and calculating the quality such as the nitrogen content rates.

The function of the measuring means 30 constructed as above is explained hereinafter. When, after a sample leaf 43 is inserted in the measuring means 30, the top cover 31 is pressed down, the signal from the switch 48 is transmitted to the CPU board 53. From the CPU board 53, a signal is outputted to the light emitting means 51, and the light emission signal is transmitted from the light emitting means 51 to the light source section 32. In this way, the light is irradiated on the sample leaf 43 alternately from the LED 34 and the LED 35. The light emitted from the LEDs 34, 35 turn, through the narrow band filters 36, 37, to the light of special wavelengths, that is, the light of near infrared ray region and visible ray region. Since the light reaches the light amount detection device 44 from the diffusion transmission plate 42 while repeating reflection and diffusion as already explained, the light is irradiated on the sample leaf 43 in the same degree of uniformity as in an integral sphere.

When the light is irradiated on the sample leaf 43, its reflection light and transmission light are received by the light amount detection means 44 separately for each of the LEDs 34, 35, and the received light signal is communicated to the analog board 50 for A/D conversion. The A/D conversion is made at the analog board 50 and the signal converted is inputted into the CPU board 53 via the I/O board 52. At the CPU board 53, from the transmission light or the reflection light of the sample leaf 43, the reflectance, transmissivity, or absorbency is calculated, and the values calculated are stored in RAM 61. Based on the absorbency stored in RAM 61 and the relation formula for obtaining the nitrogen content rate stored in advance in ROM 60, it is possible to calculate the nitrogen content rate of the measured leaf. The input section 55 is provided with a power source switch 55a for switching the measuring means 30, a measuring switch 55 enabling to measure the transmission light, and a reading-out switch 55c equipped with function of reading-out switching of a calibration curve (formula) stored in ROM 60, or absorbency or transmission light data or calculation results stored in RAM 61, or sample numbers.

Hereunder a first embodiment of the invention dealing with a diagnosis of crop in fields based on first crop information and second crop information is explained. By camera 2, the measurement is made of reflection light and of, for example, an amount of reflection light of a wavelength having relation to the nitrogen content rate, which is crop information subject to increase and decrease depending on the growth of rice plant from the field 1 under exposure to natural light. As shown in FIG. 2 to FIG. 4, in the data processing unit 20, the reflectance is calculated based on the amount of reflection light of leaves within the light receiving range measured by the camera 2 and on a formula for obtaining the reflectance within the light receiving range stored in ROM 28 and, by the reflectance thus obtained and the first crop related formula stored in ROM 28, the nitrogen content rate within the light receiving range of the camera 2 which is the first crop information, and the nitrogen content rate is stored in RAM 29.

Next, explanation is made in respect of a case where the nitrogen content rate of the leaves of the rice plant growing within the light receiving range of the camera 2. The nitrogen content rate (second crop information) of the leaves of the rice plant measured by a unit 30 is measured value obtained directly from the leaves of the rice plant, and this value is one which has not been influenced by such factors as a measurement direction and a planting density. Therefore, according to the present invention, a difference between the first crop information and the second crop information. For example, assuming that the first crop information measured first is 4.0% and the second crop information measured by the unit 30 is 3.0%, the value by the unit 30 is made the second crop information and stored in RAM 61. The second crop information obtained by the measurement unit 30 is forwarded to the data processing unit 20 from a connecting port 56 of the measurement unit 30 via an I/F board of the data processing unit 20, and this information is stored in RAM 29. At the unit 20, based on the difference of −1% between the first crop information and the second crop information in RAM 29, the first crop information is compensated to 3.0% by adding −1% to the first crop information.

That is, the difference is newly stored in RAM 29 as a compensating value, and the difference of −1% is added to compensate all the values calculated by unit 20 after the measurement by the camera 2 of the reflection light of other crop leaves within the light receiving range. In this way, the measurement not influenced by the measurement direction and the planting density is realized the camera 2 and the unit 20. Moreover, after the storing of the compensating value in RAM 29, the measurements for a number of times by the unit 30 are rendered unnecessary at least for the same field, and only one time measurement by the camera 2 results in such a high precision measurement which has not been the case ever before. Further, the measurement of nitrogen content rate by the measurement unit 30 is not necessary to be conducted with respect to all the crop leaves within the field, but it is sufficient to measure the same with respect to a representative crop leaf within the field.

A second embodiment of the invention for diagnosis is hereinafter explained. By camera 2, the measurement is made of reflection light from the reference plate 3 and of, for example, an amount of reflection light of a wavelength having relation to the nitrogen content rate, which is crop information subject to increase and decrease depending on the growth of rice plant from the field 1 under exposure to natural light. As shown in FIG. 2 to FIG. 4, in the data processing unit 20, the reflectance is calculated based on the amount of reflection light in divided sections No.①–No.⑨ measured by the camera 2 and on a formula for obtaining the reflectance for each section stored in ROM 28 and, by the reflectance thus obtained and the first crop related formula stored in ROM 28, the nitrogen content rate on a section to section basis which is the first crop information, and the nitrogen content rate is stored in RAM 29.

By the operator or by the unit 20, the nitrogen content rates of arbitrary two sections out of the rates obtained here on a section to section basis are selected, preferably the selected sections being ones in which the value of nitrogen content rate is maximum and the value of nitrogen content rate is minimum. In the sections selected as in FIG. 8 or FIG. 9, the measurement is made by the measurement unit 30 for the nitrogen content rate of leaves of the rice plant growing in the sections of the field corresponding, for example, to the section No.⑤ in which the value as being 4.2% is maximum and to the section No.⑦ in which the value as being 3.6% is minimum. The nitrogen content rates measured here are ones derived without receiving any influence from the measuring direction or from the planting density.

In the measurement unit 30, from the amount of received light obtained directly from the leaf blade of the rice crop corresponding to the two sections selected in the field described above by irradiating the light of the wavelength having relation to the leaf blade nitrogen content rate which is crop information subject to increase or decrease depending on the growth of the crop, the nitrogen content rate relating to the above two sections is calculated based on the absorbency which, in this embodiment, is converted from the amount of the received light, and the second crop related formula predetermined for obtaining the leaf blade nitrogen content from the absorbency. Then, the nitrogen content rates of 3.0% for No.⑤ section and of 2.4% for No.⑦ section are obtained, and these values are stored in RAM 29 as the second crop information. Each of the nitrogen content rates for the two sections obtained by the measurement unit 30 is forwarded to the data processing unit 20 from a connecting port 56 of the measurement unit 30 via an I/F board of the data processing unit 20, and this information is stored in RAM 29.

Figure 13:
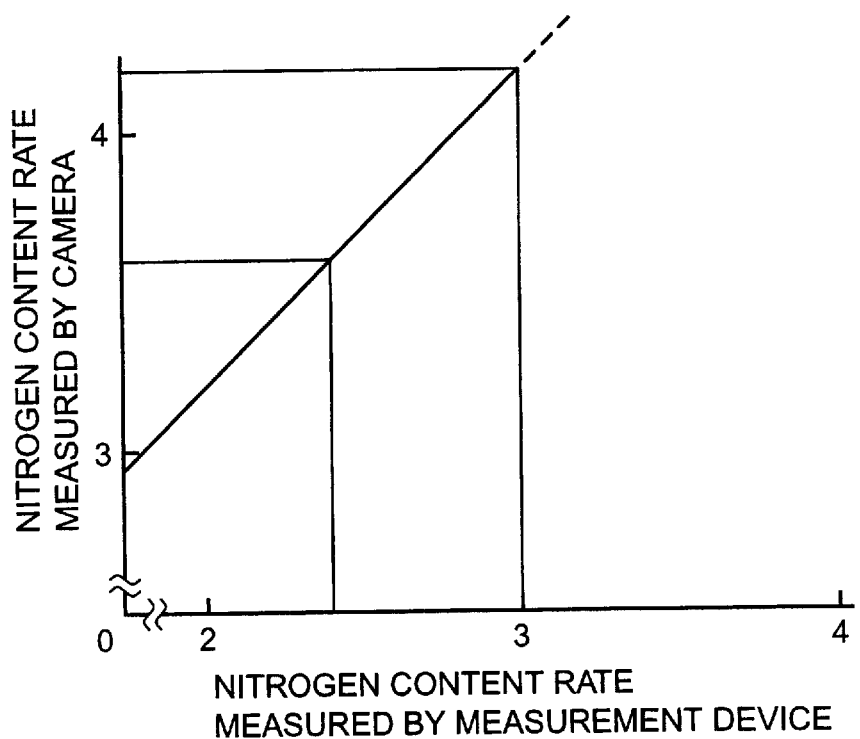
FIG. 13 is a graph showing relation of nitrogen contents between the measuring by the leaf blade nitrogen content measuring means and the image-taking by camera.
Figures 14, 15:
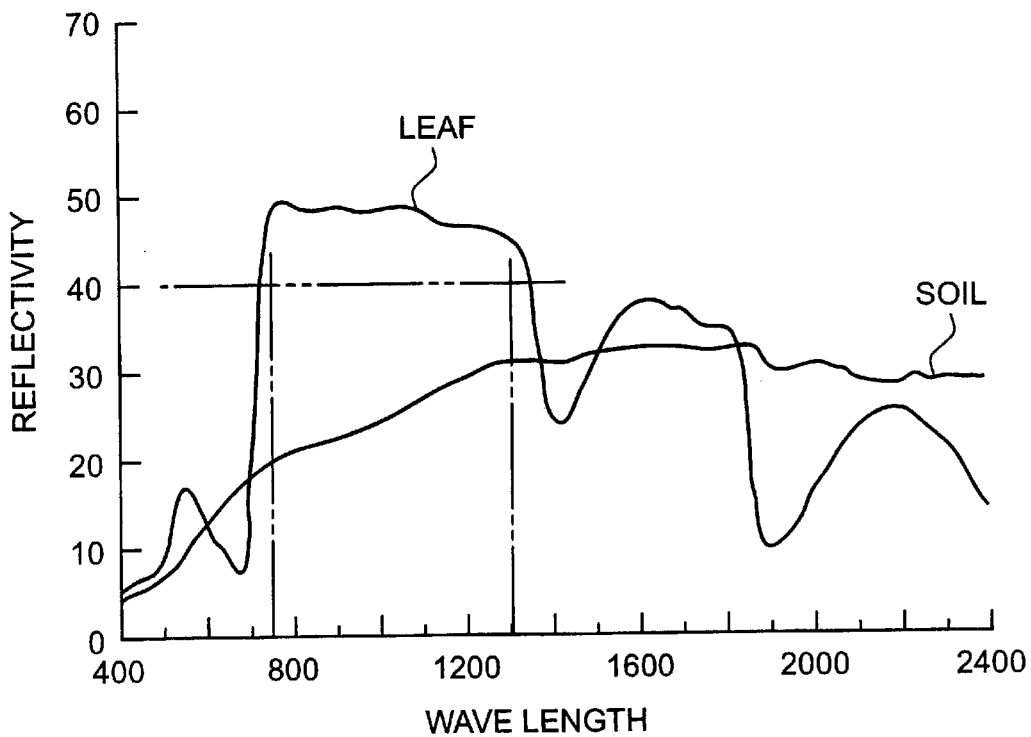
FIG. 14 is a table showing, in a plurality of divisions, values by compensation for nutritious diagnosis.
FIG. 15 is a graph showing reflectance curves with respect to wavelengths of crop leaves and soil.

With reference to FIG. 13, explanation is made on the third crop information which is obtained, based on the nitrogen content rates for the two sections constituting the second crop information stored in RAM 29, by compensating the first crop information stored also in RAM 29 for each of the sections (nitrogen content rates in sections No.①–No.⑨). FIG. 13 is a graph in which the nitrogen content rate (second crop information) measured by the measurement unit 30 is shown in the axis of abscissa while the nitrogen content rate (first crop information) calculated by the data processing unit 20 is shown in the axis of ordinate. That is, the graph represents the nitrogen content rates of 3.0% and 2.4% for two sections measured by the measurement unit 30, and the nitrogen content rates of 4.2% for No.⑤ section and of 3.6% for No.⑦ section calculated by the data processing unit 20. In this way, by the nitrogen content rates for two sections measured actually and directly from the leaf blades of the rice crop by the measurement unit 30 and the straight line represented by the simple function constituted by the relationship with the nitrogen content rates measured by the camera 2, the interrelation is made clear, and by this simple function, the nitrogen content rates measured by the camera 2 are compensated. Here, the compensation is made by the straight line represented by the function, and this function is stored in RAM 29 as a compensation conversion formula. In FIG. 14, specifically, the nitrogen content rate of 4.2% for No.⑤ section is compensated to 3.0%, and the nitrogen content rate of 3.6% for No.⑦ section is compensated to 2.4%. Similarly, as shown in FIG. 14, the values for other sections are compensated based on the compensation conversion formula determined by the interrelation of the two sections. This is how the third crop information is obtained. The third crop information thus obtained is for the nine sections but, by obtaining from this a further average value, it is possible to treat it as single crop information for the range for which the image was taken by the camera. As for the compensation coefficient, the value represented by the simple function using the representative value of the two sections has been shown, but this compensation coefficient may well be an interrelation coefficient obtained by using the crop information of the overall sections image-taken by the camera as an explanatory variable and the crop information of the overall sections obtained by the measurement unit 30 as an objective variable, and such coefficient can be utilized whether linearly or non-linearly.

Subsequently the nitrogen content rate measured by the camera 2 is compensated based on the compensation conversion formula as in FIG. 13 by the data processing unit 20 so that the resulting value can be used as a value enhancing a more precise measurement. Therefore, as compared with the conventional method in which, only by the measurement unit 30, the nitrogen content rate is measured of the leaf blades from a plurality of fields, it is possible to obtain faster the information being sought. Further, when taken into account the fact that the obtaining of the nitrogen content rate of the crop by image-taking of the reference plate and the field is still under a researching stage, it must be considered that the method described above will greatly contribute to the enhancement of the precision in the measurement. The measurement of the nitrogen content rate by the measurement unit 30 is not conducted for all the leaves of the crop in the field 1, but may be conducted only for representative leaves in the field 1.

It is obvious that the crop information to be obtained from the field 1 according to the first and second embodiments of the invention for nutritious diagnosis defers depending on the position of the camera 2 with respect to the object. That is, the field 1 here may be one field divided by a commonly called "furrow" or may be larger than the one field in area. What is important in defining the compensation value or the compensation coefficient is that the source of the crop information obtained by the camera and source of the crop information obtained by the measurement unit 30 is from the same field. As to the section in the second embodiment of the invention for the nutritious diagnosis, it does not matter whether the crop information obtained from the one field for which the image is taken by one image-taking action is divided into a plurality of sections, or the crop information obtained from a field smaller than the one field is divided into a plurality of sections. However, it is important that, in defining the compensation value or the compensation coefficient, the crop information collected is based on the same source.

A third embodiment of the invention for diagnosis is hereinafter explained. Here, as a method for obtaining the information for a plurality of sections divided from the field 1, the amount of reflection light is obtained by the camera 2 by the same number of image-taking actions as the number of the plurality of sections. That is, the difference from the second embodiment for diagnosis is that the crop information is obtained by the camera 2 individually for respective sections. In this way, since the amount of the crop information obtained on a section to section basis is larger than that obtained by one time image-taking according to the second embodiment, the precision of the compensation coefficient defined by the interrelation with respect to the crop information by the measurement unit 30 is enhanced. The compensation coefficient here may be interrelation coefficient obtained by making the crop information of all sections image-taken by the camera as an explanatory variable and the crop information of all sections obtained by the measurement unit 30 as an objective variable. The fact that such coefficient can be utilized whether linearly or non-linearly is the same as in the second embodiment.

Subsequently the nitrogen content rate measured by the camera 2 is all compensated based on the compensation conversion formula as in FIG. 13 by the data processing unit 20 so that the resulting value can be used as a value which enhances a more precise measurement. Therefore, as compared with the conventional method in which, only by the measurement unit 30, the nitrogen content rate is measured of the leaf blades from a plurality of fields, it is possible to obtain faster the information being sought. Further, when taken into account the fact that the obtaining of the nitrogen content rate of the crop by image-taking of the reference plate and the field is still under a researching stage, it must be considered that the method described above will greatly contribute to the enhancement of the precision in the measurement. The measurement of the nitrogen content rate by the measurement unit 30 is not conducted for all the leaves of the crop in the field 1, but may be conducted only for representative leaves in the field 1.

It is obvious that the crop information to be obtained from the field 1 according to the third embodiment of the invention for nutritious diagnosis defers depending on the position of the camera 2 with respect to the object. That is, the field 1 here may be one field divided by what is commonly called "furrow" or may be larger than the one field in area. What is important in defining the compensation value or the compensation coefficient is that the source of the crop information obtained by the camera and source of the crop information obtained by the measurement unit 30 is from the same field and the same section. Further, as to the section in the embodiment of the invention, it does not matter whether the crop information obtained from the one field image-taken by one image-taking action is taken as the one section, or the crop information obtained from a field smaller than the one field is taken as the one section. However, it is important that, in defining the compensation value or the compensation coefficient, the crop information collected is based on the same source.

As clarified by the foregoing, the image taken by the camera 2 can be compensated by area compensation, depression compensation and the field distance compensation. That is, errors caused by weather may be compensated by using the reference plate 3 and errors caused by the measuring direction and the planting density may be compensated by using the values in the measuring means 30. That is, even when the image is taken of the field on the ground with the camera being inclined, compensation is possible according to the present invention. Also, when the compensation is made by the measuring means 30, since, in the measurement by the camera 2, the compensation value compensating the weather errors by the reference plate caused by weather is compensated by the value obtained by directly measuring the crop leaves measured by the same camera 2 and, since the value with which the crop leaves are directly measured by the values of the measuring means 30 is a value obtained irrespective of the measuring direction and the planting density, the value finally obtained by the compensation is a value not having been influenced by various external factors unlike in the so-called remote sending where only a conventional camera 2 and data processing are used.

In collecting the crop information by the camera 2 in the above embodiments, the information obtained by the camera 2 is not necessarily all crop information. That is, when the data in each of the image elements is examined, it is found that, while almost all are crop information, it is possible that, depending on the planting density, the soil is included in the image, since the crop information is obtained in the state in which the crop is being looked down. Thus, according to the invention, the image elements received as the crop information and the image elements received as other than the crop information are separated, and only the data of the image elements received as the crop information is taken as the crop information.

Figure 16A:
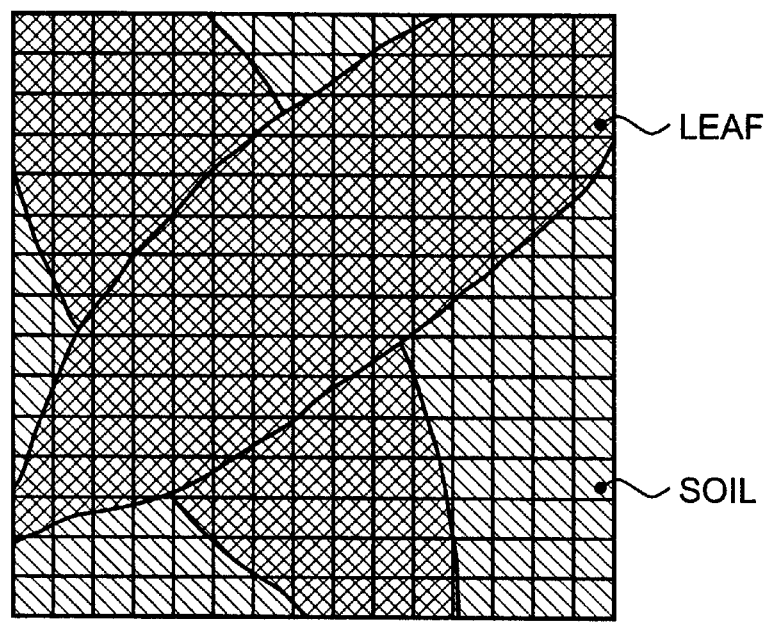
FIG. 16 is a figure showing the data of the light received from the crop leaves and the soil obtained by the camera.
Figure 16B:
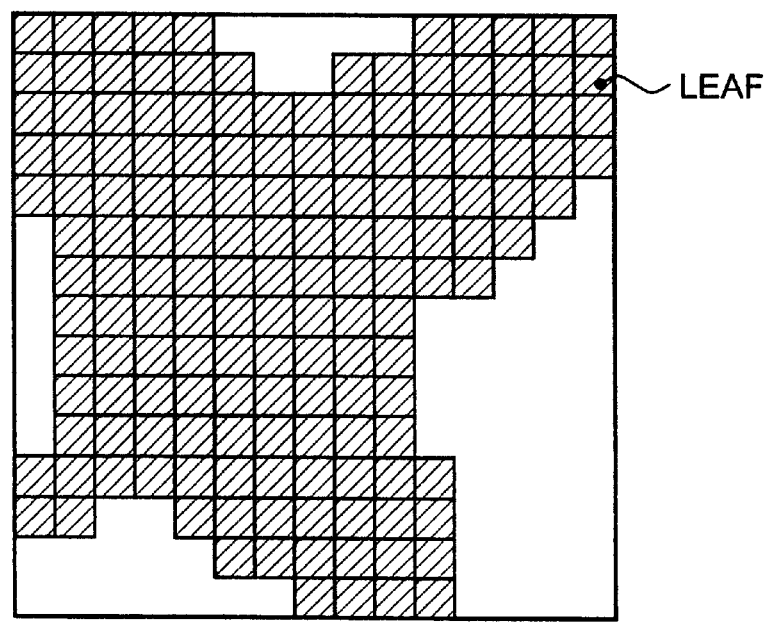

FIG. 15 is a graph showing changes with respect to the wavelengths in reflectance of the soil and in reflectance of the crop leaf. In the wavelengths of 750 nm–1300 nm, it has been found that the difference in the order of 20% occurs in the reflectance of the crop leaf with respect to the reflectance of the soil. Thus, the reflectance obtained by Formula 1 and Formula 2 showing, for example, a value exceeding 40%, is treated as the data of the light received from the crop leaf. On the other hand, a value below the above percentage is treated as not being the data of the light received from the crop leaf and is cancelled. Only the data of the light received exceeding 40% is utilized as it is, or utilized after obtaining an average value for each image element, and the value is treated as being the crop information obtained by the camera 2. For example, FIG. 16(*a*) assumes that the data of the light received are in a plurality of image elements. In this case, for a unit of 1 pixel, a portion represented by slanted grids is reflection light from the crop leaf and its reflectance is above 40%. If the portion of the slanted grids is for the soil other than the crop leaf and, if the calculation shows that the reflectance is below 40%, the data of the received light of the image element whose reflectance is below 40% is cancelled, and the data useful as the crop information is the data of the received light obtained from the image elements shown by slanted stripes as shown in FIG. 16(*b*). In this way, according to the present invention, the selection of the data of the received light by the camera 2 has been added to the determination of the compensation value or compensation coefficient based on the crop information through the camera 2 and the crop information through the measuring means 30. Thus, the information selectively obtained by the camera 2 is information obtained only from the crop leaves. The information obtained from the measuring means 30 is, of course, information directly measured from the crop leaves so that the diagnosis of the crop made by the crop information and the compensation value or the compensation coefficient is accurate and precise.

Figure 17:
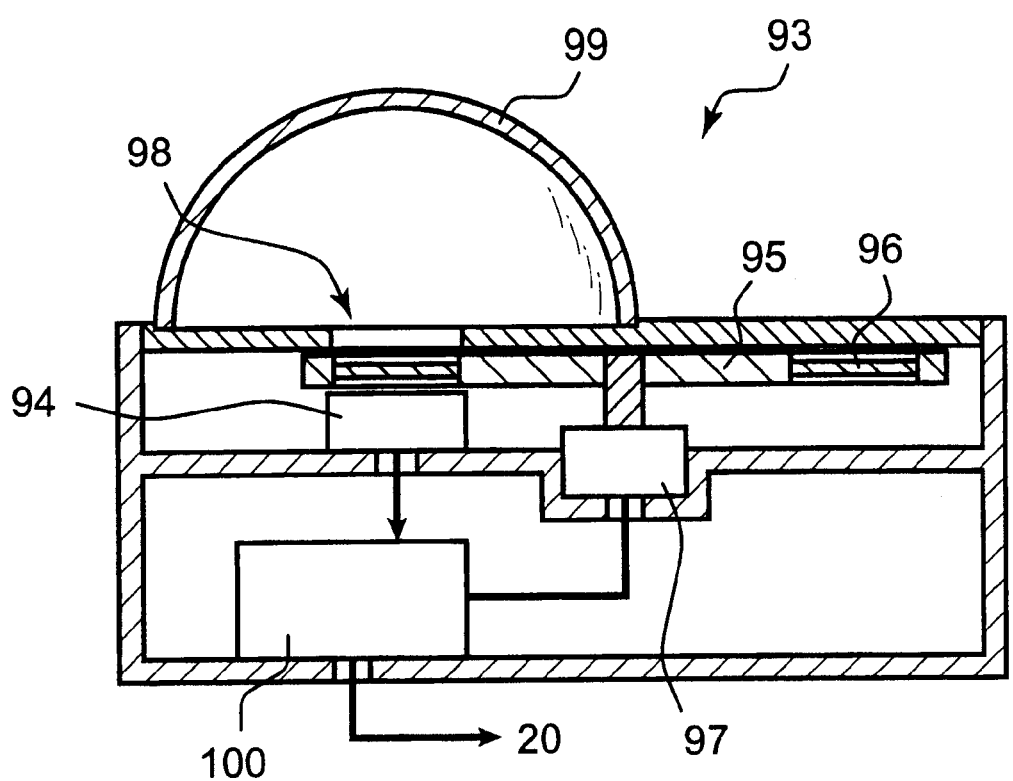
FIG. 17 is a side sectional view diagrammatically showing an illuminometer for measuring incident light.

It has been explained that the measuring of the reflection light of the crop leaves by the camera 2 is obtained by measuring the reflection light of the reference plate, but it is possible to measure the incident light in the form of the measurement by an illuminometer. FIG. 17 diagrammatically shows the illuminometer 93. This illuminometer is equipped with a photoelectric conversion section (silicon sensor) 94 having spectrum characteristics from near infra-red ray regions to visible ray regions, and a plurality of narrow band filters 96 for selecting the light incident to the photoelectric conversion section 94 are provided to the peripheral portion of the filter wheel 95 which is rotated by the stepping motor 97. By rotating this filter wheel 95, the plurality of filters 96 are switched. At the light receiving surface side (upper portion in FIG. 16) of the photoelectric conversion section 94, there is provided an opening section 98 in a shielding plate and, above this, there is provided a diffusion dome 99 formed by a diffusion reflection plate with the photoelectric conversion section 94 being in the center. The photoelectric conversion section 94 and the stepping motor 97 are communicated to a control section 100 which rotates the stepping motor 97 for switching the filters 96 and outputs signals of the photoelectric conversion section. As to the kinds of the filters 96, they are the same as those of the filters 5 of the camera 2. The control section 100 is connected to and controlled by an I/O port 25 (FIG. 3) of the data processing means 20. The filters 96 include a filter which shields the light and, in this way, zero compensation is enabled by the switching of the filters 96.

By the signal from the data processing means 20, the control section 100 of the illuminometer 93 switches the filter 96 to the intended filter. At this time, the amount of the natural light which diffusion-reflects and enters from the diffusion dome 99 is detected through the filter 96, and the signal detected by the photoelectric conversion section 94 is transmitted to the data processing means 20. At the data processing means 20, the amount of light obtained by the illuminometer 93 is made the incident light amount Y in place of the reference plate reflection light amount and is applied to Formula 5, thus resulting in Rij=P"ij/Y so that the reflection light amount obtained from the crop leaves can be calculated into the reflectance. When the illuminometer 93 is used, the first crop related formula can be obtained based on the reflectance of the time when the illuminometer 93 is made the reflection light amount.

It is possible for the one entire field to be image-taken with the compensation being made similarly, and it is possible to make the measurement at each special time period such as a panicle initiation stage which is the growth period of the rice crop, or it is possible to make compensation for a part of the field and estimate the nitrogen content for the entire field. In this method, the compensation may be more effective if it is conducted on a kind to kind basis, or a district to district basis (or a field to field basis). That is, if ROM 28 stores a plurality of compensation calibration curves separately for individual kinds or individual districts, they may be read out and used every time the need arises. The camera used in the embodiments has resolution of 240,000 pixels. If the field of 10 ares is to be image-taken at a time for obtaining the crop information, the image elements are 250 pixels per one square meter.

For the nitrogen content rate in the field as discussed above, it has been conventionally researched for the rice crop on a kind to kind basis or a district to district basis as to the best nitrogen content rate at arbitrary growth periods such as panicle initiation stage and reduction division stage. It is possible to compare the nitrogen content rate by the compensated first crop information or third crop information obtained according to the invention and the nitrogen content rate which the conventional research has determined as being reference along with the growth of the crop. When the comparison is made against such reference, whether the nitrogen content rate is above or below becomes clear, and it is possible to decide accordingly the amount of the subsequent fertilization. What has been described above is applicable to the color values of the leaves. Since, between the color values and the nitrogen content rates in the leaf blades, there are very high interrelations, and changes in the both are similar to each other. Thus, the explanations and discussions made in the foregoing may be considered applicable to any embodiments relating to the color values of the leaves. The methods explained with reference to FIG. 1 to FIG. 3 are applicable to other than the nitrogen content rate and the color values, such as height of a plant, a dry plant weight, and nitrogen absorbent amount, and are also applicable to plant other than the rice crop.

Even though the field is image-taken from the ground for the nutritious diagnosis of the field, it is possible to compensate the difference in the image-taken area for each image element caused by the depression angle and the image angle which occur when the camera is directed to the field and, since the reflection light amount is matched to the fixed area or predetermined area, the image-taking from the ground is sufficiently reliable for conducting the nutritious diagnosis of the crop.

Also, a camera which has a small number of image elements may be used and, even when there occurs difference in the sizes of the image-taken area per image element, the image elements are divided so that, by making the areas to become respectively the same, or by making the area to become a predetermined size of area, the divided area can be made a fixed area and the data of each image element can be effectively utilized.

The nutritious diagnosis of the crop can be made in a simple and easy way of calculating the nitrogen content of the crop by measuring the reflection light of crop leaves, and in addition the nutritious diagnosis of the crop can be made precisely and accurately by calculating the nitrogen content rate of the crop by directly irradiating the crop leaves and measuring the reflection light or the transmission light.

Also, in the simple and easy nutritious diagnosing method of the crop by measuring the reflection light from the crop leaves and calculating the nitrogen content in the crop, any errors caused by the measuring direction, quivering of leaves in wind, difference in planting density can be compensated by excellent precision with which the measuring of the reflection light or the transmission light by directly irradiating the crop leaves is made, and the diagnosing the crop by calculating the nitrogen content of the crop is made. By the simply and easy method of diagnosing the crop, it is made possible to carry out the diagnosis with a higher precision than that obtained by the conventional methods.

What is claimed is:

1. A method of diagnosing nutritious condition of crop in a plant field, comprising the steps of:

locating a camera equipped with a plurality of image elements in a predetermined central depression angle with respect to said plant field;

obtaining an amount of reflection light of a crop leaf for each image element by image-taking said field;

obtaining an image-taken area for each unit image element by an area function constituted by a conversion variable including a ground clearance, an image element depression angle, the number of image elements and a field angle of the camera;

making an area compensation of the amount of reflection light for each image element by said image-taken area;

making a depression angle compensation of the amount of reflection light by a depression angle coefficient predetermined for compensating differences of amounts of reflection light correspondingly with image element depression angles;

measuring an amount of light incident on said crop leaf;

obtaining reflectance from the amount of the reflection light compensated and the measured amount of incident light;

obtaining first crop information in a predetermined area based on said reflectance and a first crop related formula predetermined for obtaining crop information from reflectance, and storing said first crop information; and determining a nutritious condition of the crop in the plant field based on said first crop information.

2. A method of diagnosing nutritious condition of crop in a plant field according to claim 1, further comprising the steps of:

irradiating crop in same plant area;

measuring an amount of at least either of transmission light or reflection light which is subject to increase or decrease depending on growth of the crop and which has a wavelength having relation to the crop information;

obtaining second crop information based on the measured amount of light and a second crop related formula predetermined for obtaining crop information from amount of light, and storing said second crop information; and determining the nutritious condition of the crop in the plant field based on said first and second crop information.

3. A method of diagnosing nutritious condition of crop in a plant field, comprising the steps of:

locating a camera equipped with a plurality of image elements in a predetermined central depression angle with respect to the plant field;

obtaining an amount of reflection light of a crop leaf for each image element by image-taking said field;

obtaining an image-taken area for each unit image element by an area function constituted by a conversion variable including a distance of field of view, an image element depression angle, the number of image elements and a field angle of the camera;

making an area compensation of the amount of reflection light for each image element by said image-taken area;

making a depression angle compensation of the amount of reflection light by a depression angle coefficient predetermined for compensating differences of amounts of reflection light correspondingly with image element depression angles;

measuring an amount of light incident on said crop leaf;

obtaining reflectance from the amount of the reflection light compensated and the measured amount of incident light;

obtaining first crop information in a predetermined area based on said reflectance and a first crop related formula predetermined for obtaining crop information from reflectance, and storing said first crop information; and determining a nutritious condition of the crop in the plant field based on said first crop information.

4. A method of diagnosing nutritious condition of crop in a plant field according to claim 3, further comprising the steps of:

irradiating crop in same plant area;

measuring an amount of at least either of transmission light or reflection light which is subject to increase or decrease depending on growth of the crop and which has a wavelength having relation to the crop information;

obtaining second crop information based on the measured amount of light and a second crop related formula predetermined for obtaining crop information from amount of light, and storing said second crop information; and determining the nutritious condition of the crop in the plant field based on said first and second crop information.

5. A method of diagnosing nutritious condition of crop in a plant field, comprising the steps of:

locating a camera equipped with a plurality of image elements in a predetermined central depression angle with respect to the plant field;

obtaining an amount of reflection light of a crop leaf for each image element by image-taking the field;

obtaining an image-taken area for each unit image element by an area function constituted by a conversion variable including a ground clearance, an image element depression angle, the number of image elements and a field angle of the camera;

making an area compensation of the amount of reflection light for each image element by said image-taken area;

dividing a plurality of image elements into sections based on the image-taken area of the unit image element corresponding to the maximum area among the image-taken areas obtained for each unit image element;

obtaining reflectance from the amount of reflection light for each section and the amount of light incident on the crop leaf;

obtaining first crop information in a predetermined area based on said reflectance and a first crop related formula predetermined for obtaining crop information from reflectance, and storing said first crop information; and determining a nutritious condition of the crop in the plant field based on said first crop information.

6. A method of diagnosing nutritious condition of crop in a plant field, comprising the steps of:

locating a camera equipped with a plurality of image elements in a predetermined central depression angle with respect to the plant field;

obtaining an amount of reflection light of a crop leaf for each image element by image-taking the field;

obtaining an image-taken area for each unit image element by an area function constituted by a conversion variable including a ground clearance, an image element depression angle, the number of image elements and a field angle of the camera;

making an area compensation of the amount of reflection light for each image element by said image-taken area;

obtaining reflectance from the amount of reflection light of the unit image element below the predetermined image-taken area among the image-taken areas obtained for the respective unit image elements and the amount of light incident on the crop leaf;

obtaining first crop information in a predetermined area based on said reflectance and a first crop related formula predetermined for obtaining crop information from reflectance, and storing said first crop information; and determining a nutritious condition of the crop in the plant field based on said first crop information.

7. A method of diagnosing nutritious condition of crop in a plant field, comprising the steps of:

locating a camera equipped with a plurality of image elements in a predetermined central depression angle with respect to the plant field;

obtaining an amount of reflection light of a crop leaf for each image element by image-taking the field;

obtaining an image-taken area for each unit image element by an area function constituted by a conversion variable including a distance of field of view, an image element depression angle, the number of image elements and a field angle of the camera;

making an area compensation of the amount of reflection light for each image element by said image-taken area;

dividing a plurality of image elements into sections based on the image-taken area of the unit image element corresponding to the maximum area among the image-taken areas obtained for each unit image element;

obtaining reflectance from the amount of reflection light for each section and the amount of light incident on the crop leaf;

obtaining first crop information in a predetermined area based on said reflectance and a first crop related formula predetermined for obtaining crop information from reflectance, and storing said first crop information; and determining a nutritious condition of the crop in the plant field based on said first crop information.

8. A method of diagnosing nutritious condition of crop in a plant field, comprising the steps of:

locating a camera equipped with a plurality of image elements in a predetermined central depression angle with respect to the plant field;

obtaining an amount of reflection light of a crop leaf for each image element by image-taking the field;

obtaining an image-taken area for each unit image element by an area function constituted by a conversion variable including a distance of field of view, an image element depression angle, the number of image elements and a field angle of the camera;

making an area compensation of the amount of reflection light for each image element by said image-taken area;

obtaining reflectance from the amount of reflection light of the unit image element below the predetermined image-taken area among the image-taken areas obtained for the respective unit image elements and the amount of light incident on the crop leaf;

obtaining first crop information in a predetermined area based on said reflectance and a first crop related formula predetermined for obtaining crop information from reflectance, and storing said first crop information; and determining a nutritious condition of the crop in the plant field based on said first crop information.

9. A method of diagnosing nutritious condition of crop in a plant field according to claim 5, further comprising the steps of:

irradiating crop in same plant area;

measuring an amount of at least either of transmission light or reflection light which is subject to increase or decrease depending on growth of the crop and which has a wavelength having relation to the crop information;

obtaining second crop information based on the measured amount of light and a second crop related formula predetermined for obtaining crop information from amount of light, and storing said second crop information; and determining the nutritious condition of the crop in the plant field based on said first and second crop information.

10. A method of diagnosing nutritious condition of crop in a plant field according to claim 6, further comprising the steps of:

irradiating crop in same plant area;

measuring an amount of at least either of transmission light or reflection light which is subject to increase or decrease depending on growth of the crop and which has a wavelength having relation to the crop information;

obtaining a second crop information based on the measured amount of light and a second crop related formula predetermined for obtaining crop information from amount of light, and storing said second crop information; and determining the nutritious condition of the crop in the plant field based on said first and second crop information.

11. A method of diagnosing nutritious condition of crop in a plant field according to claim 7, further comprising the steps of:

irradiating crop in same plant area;

measuring an amount of at least either of transmission light or reflection light which is subject to increase or decrease depending on growth of the crop and which has a wavelength having relation to the crop information;

obtaining a second crop information based on the measured amount of light and a second crop related formula predetermined for obtaining crop information from amount of light, and storing said second crop information; and determining the nutritious condition of the crop in the plant field based on said first and second crop information.

12. A method of diagnosing nutritious condition of crop in a plant field according to claim 8, further comprising the steps of:

irradiating crop in same plant area;

measuring an amount of at least either of transmission light or reflection light which is subject to increase or decrease depending on growth of the crop and which has a wavelength having relation to the crop information;

obtaining a second crop information based on the measured amount of light and a second crop related formula predetermined for obtaining crop information from amount of light, and storing said second crop information; and determining the nutritious condition of the crop in the plant field based on said first and second crop information.

* * * * *